(12) United States Patent
Maihle et al.

(10) Patent No.: US 7,638,303 B2
(45) Date of Patent: Dec. 29, 2009

(54) SOLUBLE ERBB3 RECEPTOR ISOFORMS

(75) Inventors: Nita J. Maihle, New Haven, CT (US); Hakjoo Lee, Pittsford, NY (US)

(73) Assignee: Tumor Biology Investment Group, Inc., Lexington, KY (US)

( * ) Notice: Subject to any disclaimer, the term of this patent is extended or adjusted under 35 U.S.C. 154(b) by 0 days.

(21) Appl. No.: 12/144,166

(22) Filed: Jun. 23, 2008

(65) Prior Publication Data
US 2008/0274504 A1   Nov. 6, 2008

Related U.S. Application Data

(62) Division of application No. 10/159,353, filed on May 31, 2002, now Pat. No. 7,390,632.

(60) Provisional application No. 60/294,824, filed on May 31, 2001.

(51) Int. Cl.
*C07K 14/00* (2006.01)
*C07H 21/02* (2006.01)
*C07H 21/04* (2006.01)
*C12N 1/00* (2006.01)
*C12N 5/00* (2006.01)
*C12N 5/02* (2006.01)
*C12N 15/00* (2006.01)
*C12P 21/06* (2006.01)

(52) U.S. Cl. .................. 435/69.1; 435/320.1; 435/243; 435/325; 530/350; 536/23.1; 536/23.5

(58) Field of Classification Search .................. None
See application file for complete search history.

(56) References Cited

U.S. PATENT DOCUMENTS 5,183,884 A   2/1993   Kraus

OTHER PUBLICATIONS

Junttila, T.T. et al.,ErbB4 and Its Isoforms Selective Regulation of Growth Factor Responses by Naturally Occurring Receptor Variants Trends, Cardiovasc Med 10: 304-310 (2000).

(Continued)

*Primary Examiner*—Cherie M Woodward
(74) *Attorney, Agent, or Firm*—Cohen & Grigsby, P.C.

(57) ABSTRACT

The present invention discloses a method using human soluble ErbB3, for example p85-sErbB3, as a negative regulator of heregulin-stimulated ErbB2, ErbB3, and ErbB4 activation. The present invention also discloses p85-sErbB3 binding to heregulin with an affinity comparable to that of full-length ErbB3, and competitively inhibiting high affinity heregulin binding to ErbB2/ErbB3 heterodimers on the cell surface of breast carcinoma cells. The present invention also uses p85-sErbB3 to inhibit heregulin-induced phosphorylation of ErbB2, ErbB3, and ErbB4 in cells, as a negative regulator of heregulin-stimulated signal transduction, and as a block for cell growth. The present invention is also directed to nucleic acids and expression vectors encoding p85-sErbB3, host cells harboring such expression vectors, and methods of producing the protein. The present invention discloses a method of therapeutically treating human malignancies associated with heregulin-mediated cell growth such as breast and prostate cancer.

10 Claims, 7 Drawing Sheets

Soluble Forms of the ErbB3 Receptor

Figure 2:
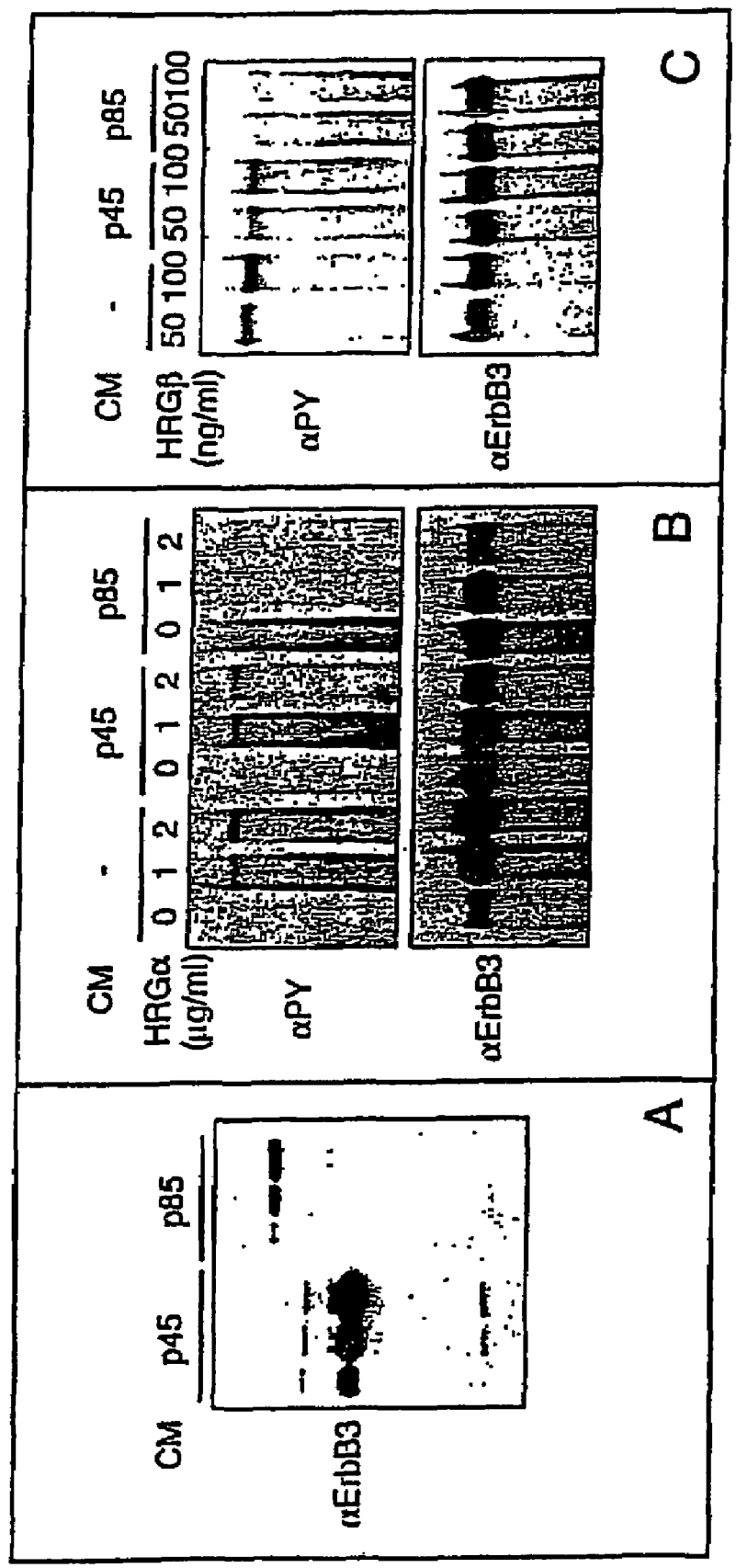

| | No. of unique amino acids | Apparent MW (kDa) |
|---|---|---|
| ErbB3-S | 43 | 22 |
| p50-ErbB3$_{R1F}$ | 30 | 50 |
| p45-ErbB3$_{R2F}$ | 2 | 45 |
| p85-ErbB3$_{R31F}$ | 24 | 85 |
| p75-ErbB3$_{R35F}$ | 41 | 75 |

OTHER PUBLICATIONS

Kvvong, K.Y. and Hung, M.C., A Novel Splice Variant of HER2 With Increased Transformation Activity, Molecular Carcinogenesis 23: 62-68 (1998).

Falls, R. et al., ARIA, ARIA, a Protein That Stimulates Acetylcholine Receptor Synthesis, Is a Member of the Neu Ligand Family, Cell 72 (5): 801-815 (1993).

Hemi, R. et al., Transactivation of ErbB3 and ErbB3 by Tumor Necrosis Factor—and Anisomycin Leads to Impaired Insulin Signaling through Serine/Threonine Phosphorylation or IRS Proteins, The Journal of biological Chemistry, 277 (2002), 8961-8969.

Alimandi, M., et al., Cooperative Signaling of ErbB3 and ErbB2 in Neoplastic Transformation and Human Mammary Carcinomas, Oncogene (1995) 10: 1813-1821.

Alroy, I., et al., The ErbB Signaling Network in Embryogenesis and Oncogenesis: Signal Diversification Through Combinatorial Ligand-Receptor Interactions, FEBS Letters, (1997) 410: 83-86.

Basu, A., et al., Inhibition of Tyrosine Kinase Activity of the Epidermal Growth Factor (EGF) Receptor by a Truncated Receptor Form That Binds to EGF: Role for Interreceptor Interaction in Kinase Regulation, Molecular and Cellular Biology, (1989) 9(2): 671-677.

Callaghan, T., et al., A Complete Description of the EGF-Receptor Exon Structure: Implication in Oncogenic Activation and Domain Evolution. Oncogene (1993) 8: 2939-2948.

Carraway, K., et al., Neuregulins and Their Receptors, Current Opinion in Neurobiology (1995) 5: 606-612.

Corfas, G. et al., Aria, A Protein that Stimulates Acetylcholine Receptor Synthesis, Also Induces Tyrosine Phosphorylation of a 185kDa Muscle Transmembrane Protein, Proc. Natl. Acad. Sci. USA, (1993) 90: 624-1628.

Doherty, J., et al., The Her-2/Neu Receptor Tyrosine Kinase Gene Encodes a Secreted Autoinhibitor, Proc. Natl. Acad. Sci. USA, (1999) 96(19): 10869-10874.

Fitzpatrick, V., et al. Formation of a High Affinity Heregulin Binding Site Using the Soluble Extracellular Domains of ErbB2 with ErbB3 or ErbB4, FEBS Letters., (1998) 431: 102-106.

Flickinger, T., W., et al., An Alternatively Processed mRNA from the Avian c-erbB Gene Encodes a Soluble, Truncated Form of the Receptor That Can Block Ligand-Dependent Transformation, Molecular and Cellular Biology, Molecular and Cellular Biology, (1992), 12(2): 883-893.

Hijazi, M. M. et al., Heregulin Regulates the Actin Cytoskelton and Promotes Invasive Properties in Breast Cancer Cell Lines, International Journal of Oncology, (2000) 17: 629-41.

Holmes, W. E., et al., Identification of Heregulin, a Specific Activator of p185erbB2, Science (1992) 256: 1205-1210.

Katoh, M., et al., c-erbB3 Gene Encodes Secreted as well as Transmembrane Receptor Tyrosine Kinase, Biochemical and Biophysical Research Communications, (1993) 192(3): 1189-1197.

Krane, I. M., et al., NDF/Heregulin Induces Persistence of Terminal End Buds and Adenocarcinomas in the Mammary Glands of Transgenic Mice, Oncogene (1996) 12: 1781-1788.

Kraus, M. H., et al., Isolation and Characterization of ERBB3, a Third Member of the ERBB/Epidermal Growth Factor Receptor Family: Evidence for Overexpression in a Subset of Human Mammary Tumors, Proc. Natl. Acad. Sci. USA, (1989) 86: 9193-9197.

Lax, I, et al., Functional Analysis of the Ligand Binding Site of EGF-Receptor Utilizing Chimeric Chicken/Human Receptor Molecules, The EMBO Journal, (1989) 8(2): 421-427.

Lee, H., et al., Isolation and Characterization of Four Alternate c-erbB3 Transcripts Expressed in Ovarian Carcinoma-Derived Cell Lines and Normal Human Tissues, Oncogene, (1998) 3243-3252.

Lewis, G. D., et al., Growth Regulation of Human Breast and Ovarian Tumor Cells by Heregulin: Evidence for the Requirement of ErbB2 as a Critical Component in Mediating Heregulin Responsiveness, Cancer Research (1996) 56: 1457-1465.

Marchionni, M. A., et al., Glial Growth Factors are Alternatively Spliced erbB2 Ligands Expressed in the Nervous System, Nature (1993) 362: 312-318.

Meyer, D., et al., Multiple Essential Functions of Neuregulin in Development, Nature (1995) vol. 378: 386-390.

Peles, E, et al., Isolation of the Neu/HER-2 Stimulatory Ligand: a 44 kd Glycoprotein That Induces Differentiation of Mammary Tumor Cells, Cell (1992) 69: 205-16.

Plowman, G. D., et al. Ligand-Specific Activation of HER4/p180erbB4, a Fourth Member of the Epidermal Growth Factor Receptor Family, Proc. Natl. Acad. Sci USA (1993) 90: 1746-1750.

Plowman, G. D., et al., Molecular Cloning and Expression of an Additional Epidermal Growth Factor Receptor-Related Gene, Proc. Natl. Acad. Sci. USA (1990) 87: 4905-4909.

Ram, T. G., et al., Blocking HER-2/HER-3 function with a Dominant Negative Form of HER-3 in Cells Stimulated by Heregulin and in Breast Cancer Cells with HER-2 Gene Amplification, Cell Growth & Differentiation, (2000) 11: 173-183.

Redemann, N., et al., Anti-Oncogenic Activity of Signalling-Defective Epidermal Growth Factor Receptor Mutants, Molecular and Cellular Biology (1992) 12(2): 491-498.

Robinson, D. et al., A Tyrosine Kinase Profile of Prostate Carcinoma, Proc. Natl. Acad. Sci. USA (1996) 93: 5958-5962.

Siegel, P. M., et al., Elevated Expression of Activated Forms of Neu/ErbB-2 and ErbB-3 are Involved in the Induction of Mammary Tumors in Transgenic Mice: Implications for Human Breast Cancer, The EMBO Journal (1999) 18(8): 2149-2164.

Singer, E., et al., Identification of a Heregulin Binding Site in HER3 Extracellular Domain, The Journal of Biological Chemistry, (2001) 276(47): 44266-74.

Sundaresan, S. et al., The Biology of Human Epidermal Growth Factor Receptor 2, Current Oncology Reports (1999) 1: 16-22.

Tsai, M. S., et al. , Expression and Function of CYR61, an Angiogenic Factor, in Breast Cancer Cell Lines and Tumor Biopsies, Cancer Research (2000) 60: 5603-5607.

Vartanian, T., et al., Axonal Neuregulin Signals Cells of the Oligodendrocyte Lineage through Activation of HER4 and Schwann Cells through HER2 and HER3, The Journal of Cell Biology (1997) 137(1): 211-220.

Wallasch, C., et al., Heregulin-Dependent Regulation of HER2/Neu Oncogenic Signaling by Heterodimerization with HER3, The Embo Journal 14(17): 4267-4275.

Wen, D., et al., Neu Differentiation Factor: A Transmembrane Glycoprotein Containing an EGF Domain and an Immunoglobulin Homology Unit, Cell (1992) 69: 559-572.

Chen, X. et al., An Immunological Approach Reveals Biological Differences Between the Two NDF/Heregulin Receptors, ErbB-3 and ErbB-4 J Biol. Chem. Mar. 29, (1996) ; 271(13) 7620-7629.

Tzahar, E. et al., ErbB-3 and ErbB-4 Function as the Respective Low and High Affinity Receptors of all Neu Differentiation Factor/Heregulin Isoforms, J Biol. Chem. (1994) 269(40): 25226-25233.

Sliwkowski, M. et al., Coexpression of erbB2 and erbB3 Proteins Reconstitutes a High Affinity Receptor for Heregulin, J.Biol. Chem. (1994) 269(20): 14661-14665.

UniProt database entry, Q9BUD7 Human, Accession No. Q9BUD7, Jun. 1, 2001.

Strausberg, R. L., et al., Generation and Initial Analysis of More than 15,000 Full-Length Human and Mouse cDNA Sequences, PNAS USA (2002) 99(26): 16899-903.

Wells, J., Addivity of Mutational Effects in Proteins, Biochemistry (1990) 29(37): 8509-8517.

Bowie, J., et al., Deciphering the Message in Protein Sequences: Tolerance to Amino Acid Substitutions, Science (1990) 247: 1306-1310.

Lee, H. et al., A Naturally Occurring Secretred Human ErbB3 Receptor Isoform Inhibits Heregulin-Stimulated Activation of ErbB2, ErbB3 and ErbB4, Cancer Research (2001) 61: 4467-4473.

Soluble Forms of the ErbB3 Receptor

| | Extracellular | TM | Intracellular | No. of unique amino acids | Apparent MW (kDa) |
|---|---|---|---|---|---|
| | I II III IV | | | | |
| ErbB3-S | | | | 43 | 22 |
| p50-ErbB3<sub>R1F</sub> | | | | 30 | 50 |
| p45-ErbB3<sub>R2F</sub> | | | | 2 | 45 |
| p85-ErbB3<sub>R31F</sub> | | | | 24 | 85 |
| p75-ErbB3<sub>R35F</sub> | | | | 41 | 75 |

FIGURE 1

SOLUBLE ERBB3 RECEPTOR ISOFORMS

This application is a divisional of U.S. application Ser. No. 10/159,353 filed May 31, 2002 now U.S. Pat. No. 7,390,632, which claims priority to U.S. Provisional Application No. 60/294,824 filed May 31, 2001, both of which are incorporated herein by reference.

The disclosed invention was made with the support of a grant from the National Cancer Institute (CA85133). The United States Government has certain rights in the invention.

FIELD OF INVENTION

Embodiments of the present invention generally pertain to methods and therapeutics that relate to soluble ErbB3 proteins (sErbB3), including p85-sErbB3, p45-sErbB3 and other isoforms of sErbB3, wherein said sErbB3 protein binds to heregulins and antagonizes heregulin-stimulated activation of the ErbB receptors and blocks the cell proliferative activity thereof. The present invention also is directed to expression vectors encoding an sErbB3 protein, including p85-sErbB3, p45-sErbB3 and other isoforms of ErbB3, host cells harboring such expression vectors, methods of preparing such proteins, and methods and systems utilizing such proteins for the treatment of conditions associated with undesired heregulin stimulation.

BACKGROUND OF THE INVENTION

The following background information is provided to assist the reader to understand the invention disclosed below and the environment in which it will typically be used. The terms used herein are not intended to be limited to any particular narrow interpretation unless clearly stated otherwise, either expressly or impliedly, in this document.

The heregulins (also called neuregulins, neu differentiation factor (NDF), acetylcholine receptor inducing activity (ARIA), glial growth factors (GGFs)) are a family of growth factors that activate members of the ErbB/EGF receptor family (Holmes, Sliwkowski et al. 1992; Peles, Bacus et al. 1992; Wen, Peles et al. 1992; Falls, Rosen et al. 1993; Marchionni, Goodearl et al. 1993). Isoforms of heregulins, all of which arise from splice variants of a single gene, NRG-1 (neuregulin-1), have been cloned and classified into the α and β subgroups based on structural differences in their EGF binding domains (Holmes, Sliwkowski et al. 1992).

ErbB-mediated signal transduction exerted by heregulins has been implicated in the regulation of diverse biological events including Schwann cell differentiation, neural regulation of skeletal muscle differentiation, heart development, and proliferation and differentiation of normal and malignant breast epithelial cells (Alroy and Yarden 1997; Sundaresan, Penuel et al. 1999). Research has shown that breast carcinoma cells respond to heregulin through proliferation, differentiation, as well as morphogenesis. Carcinoma cells expressing heregulin are hormone-independent and correlated with the ability for metastasis in experimental studies.

ErbB3 is a transmembrane glycoprotein encoded by the c-erbB3 gene (Kraus, Issing et al. 1989; Plowman, Whitney et al. 1990). The ErbB3 receptor belongs to the ErbB family which is composed of four growth factor receptor tyrosine kinases, known as ErbB1/EGFR, ErbB2/Neu, ErbB4, as well as ErbB3. ErbB3 and ErbB4 are receptors for heregulins and ErbB2 is a coreceptor (Carraway and Burden 1995). These receptors are structurally related and include three functional domains: an extracellular ligand-binding domain, a transmembrane domain, and a cytoplasmic tyrosine kinase domain (Plowman, Culouscou et al. 1993). The extracellular domain can be further divided into four subdomains (I-IV), including two cysteine-rich regions (II and IV) and two flanking regions (I and M). The ErbB3 is unusual among receptor tyrosine kinases in that its catalytic domain is defective. Despite its lack of intrinsic catalytic activity, ErbB3 is an important mediator of heregulin responsiveness. Heregulin binding induces ErbB3 to associate with other members of the ErbB family to form heterodimeric receptor complexes. ErbB3 then transactivates the kinase of its partner receptor which initiates a variety of cytoplasmic signaling cascades.

The ErbB3 receptor is important in regulating cellular growth and differentiation. Particular attention has focused on the role of ErbB3 as a coreceptor of ErbB2 in the area of cancer research. Transgenic mice that have been engineered to overexpress heregulin in mammary glands have been reported to exhibit persistent terminal end buds and, over time, to develop mammary adenocarcinomas (Krane and Leder 1996). ErbB3 expression studies on tumor tissues and on cell lines show frequent co-expression of ErbB2 and ErbB3 receptors (Alimandi, Heidaran et al. 1995; Meyer and Birchmeier 1995; Robinson, He et al. 1996; Siegel, Ryan et al. 1999). In addition, both ErbB2 and ErbB3 are activated in mammary tumors formed in transgenic mice harboring only the activated form of ErbB2 (Siegel, Ryan et al. 1999). Many cell lines used for experimental tumor formation studies are either estrogen-dependent (MCF-7 and T47D, the low ErbB2 expressers) or estrogen-independent (SKBR3, high ErbB2 expressers). However, these cell lines do not exhibit metastatic phenotypes. When MCF-7 cells are transfected to overexpress ErbB2, MCF-7 cells gain estrogen-independent phenotype, however, they never metastasize. On the other hand, the MCF-7 cells overexpressing heregulin gain metastatic phenotype, suggesting heregulin's active role in metastasis (Hijazi, Thompson et al. 2000; Tsai, Homby et al. 2000).

Five alternate ErbB3 transcripts arise from read-through of an intron and the use of alternative polyadenylation signals (Lee and Maihle 1998; Katoh, Yazaki et al. 1993). Using 3'-RACE the inventors have isolated four novel c-erbB-3 cDNA clones of 1.6, 1.7, 2.1, and 2.3 kb from a human ovarian carcinoma-derived cell line (Lee and Maihle 1998). p85-sErbB3 of 543 amino acids (aa), encoded by a 2.1 kb alternate c-erbB3 transcript (cDNA clone R31F), is composed of subdomains I through III and the first third of subdomain IV, and has a unique 24 amino acid carboxy-terminal sequence. p45-sErbB3 of 312 aa, encoded by a 1.7 kb alternate c-erbB3 transcript (cDNA clone R2F) contains subdomains I, II, and a portion of subdomain III of the extracellular domain of ErbB-3 followed by two unique glycine residues. p50-sErbB3 of 381 aa, encoded by a 1.6 kb alternate c-erbB3 transcript (cDNA clone R1F) contains subdomains I, II, and a portion of subdomain III of the extracellular domain of ErbB-3 followed by 30 unique amino acids. p75-sErbB3 of 515 aa, encoded by a 2.3 kb alternate c-erbB3 transcript (cDNA clone R35F), is composed of subdomains I through III, and has a unique 41 amino acid carboxy-terminal sequence (FIG. 1) (Lee and Maihle 1998).

Using various recombinant forms of EGFR, it has been shown that efficient inhibition of full-length EGFR activation by dominant-negative heterodimerization occurs only when these deletion mutants retain the transmembrane domain in addition to the extracellular domain (Redemann, Holzmann et al. 1992). Similarly, a recombinant dominant-negative ErbB3 mutant with a deleted cytoplasmic domain but which retains its transmembrane domain can inhibit full-length ErbB2 and ErbB3 activation (Ram, Schelling et al. 2000). In contrast, in avian tissues, expression of a naturally occurring sEGFR/ErbB1 inhibits TGFα dependent transformation (Flickinger, Maihle et al. 1992). An aberrant soluble EGFR secreted by the A431 human carcinoma cell line also has been reported to inhibit the kinase activity of purified full-length EGFR in a ligand-independent manner (Basu, Raghunath et al. 1989). In no case do these soluble EGFR/ErbB1 receptors function as antagonists through high affinity ligand-binding. Similarly, herstatin, a naturally occurring soluble ErbB2 protein which inhibits ErbB2 activation appears to function by blocking ErbB2 dimerization (Doherty, Bond et al. 1999).

The soluble ErbB3 protein, specifically the p85-sErbB3 and p45 sErbB3 isoforms, is unique among other naturally occurring ErbB receptors in that it binds specifically to heregulin with high affinity and inhibits its binding to cell surface receptors and consequently inhibits heregulin-induced activation of the receptors and their downstream effectors. Thus sErbB3, specifically p85-sErbB3 and p45-sErbB3, can be used as therapeutic reagents for heregulin-induced malignancies such as mammary and prostate tumors.

Heretofore, production and purification methods for, therapeutic uses of, and useful compositions containing, this protein, referred to herein as p85-sErbB3 have not been available.

SUMMARY OF THE INVENTION

Embodiments of the present invention pertain to several novel isolated and purified nucleic acids which encode soluble isoforms of ErbB3. Preferred embodiments of this aspect of the invention are nucleic acid sequences which specifically encode a soluble form of ErbB3 whose amino acid sequence comprises the sequence of SEQ ID NO:2 or SEQ ID NO: 4. The related nucleic acid embodiments comprise SEQ ID NO:1 and SEQ ID NO: 3.

Particular embodiments of the present invention relate to isoforms of sErbB3 that bind to HRG with high affinity and effectively block heregulin (HRG) binding to cell surface receptors. Even more particularly, the embodiments of the present invention relate to the use of p85-sErbB3 to bind to HRG with high affinity and substantially block HRG binding to cell surface receptors. Embodiments of the present invention also pertain to the diagnosis and treatment of cancer cells using p85-sErbB3 and other sErbB3 isoforms.

A preferred embodiment of the present invention pertains to an expression vector, such as a plasmid or virus, containing the isolated cDNA encoding p85-sErbB3 or other sErbB3 isoforms, as well as a cell, either eukaryotic or prokaryotic, containing the expression vector.

Embodiments of the present invention also pertain to a process for producing the p85-sErbB3 isoform and other sErbB3 isoforms, which comprises the steps of ligating the isolated DNA into an expression vector capable of expressing the isolated DNA in a suitable host; transforming the host with the expression vector; culturing the host under conditions suitable for expression of the isolated DNA and production of the p85-sErbB3 protein or other sErbB3 isoforms, and isolating the protein from the host. The host cell may be a prokaryote, or a eukaryote.

Further embodiments of the present invention relate to polyclonal or monoclonal antibodies directed against unique p85-sErbB3 or other sErbB3 isoform epitopes. Particular embodiments relate to polyclonal and monoclonal antibodies specific to p85-sErbB3 generated using a C-terminal unique sequence of the p85-sErbB3 as an antigen. The affinity-purified antibody can be used to detect p85-sErbB3 using immunoblot analysis and other detection methods.

Another embodiment of the invention relates to a system and method of detecting p85-sErbB3 and other sErbB3 isoforms in a mammalian biological specimen which is selected from the group consisting of fluids (including blood, serum, plasma, urine and ascites), tissues, and their derivatives. A particular embodiment of the present invention pertains to immunoprecipitation followed by immunoblot analysis to detect p85-sErbB3 using anti-ErbB3 antibodies.

Yet another embodiment of this invention relates to a vector for gene therapy, comprising a nucleic acid molecule having i) a transcription regulatory sequence; and ii) a second sequence coding for p85-sErbB3 or other sErbB3 isoforms under transcriptional control of the transcription regulatory sequence; and a delivery vehicle for delivering the nucleic acid molecule.

Other aspects, embodiments, features and advantages of the present invention will be apparent from reading the description of the following preferred embodiments.

BRIEF DESCRIPTION OF THE FIGURES AND DEFINITIONS

FIG. 1. Diagram of soluble ErbB3 (sErbB3) proteins. ErbB3 is composed of a 19 amino acid (aa) signal peptide sequence that is cleaved (gray box), an extracellular ligand-binding domain (aa1-620), a transmembrane domain (aa 621-646; indicated as TM), and an intracellular domain (aa 647-1323). The extracellular domain of the receptor can be further divided into four subdomains (I-IV), as noted in the text. The alternate c-erbB3 transcripts arise from read-through of an intron and the use of alternative polyadenylation signals. p45-sErbB3 contains the amino-terminal 310 amino acids of ErbB3 and two unique carboxy-terminal amino acid residues. p50-sErbB3 contains the amino-terminal 351 amino acids of ErbB3 and 30 unique carboxy-terminal amino acid residues. p75-sErbB3 contains the amino-terminal 474 amino acids of ErbB3 and 41 unique carboxy-terminal amino acid residues. p85-sErbB3 contains the amino-terminal 519 amino acids of ErbB3 and 24 unique carboxy-terminal amino acid residues. The carboxy-terminal unique sequences are denoted as black boxes.

FIG. 2. p45-sErbB3 and p85-sErbB3 in conditioned media can block HRG-induced activation of ErbB3. (A) p45-sErbB3 and p85-sErbB3 in the concentrated conditioned media were detected by Western blotting using an anti-ErbB3 antibody recognizing the extracellular region of ErbB3. Increasing volumes (5, 10, 20 μl; left to right) of the concentrated conditioned media (×15) were loaded on an SDS-PAGE gel. (B) and (C) The Ba/F3 (ErbB2+ErbB3) cells were stimulated with HRGα (panel B) and HRGβ (panel C) with or without the concentrated conditioned media for 10 min at room temperature prior to lysis. ErbB3 was immunoprecipitated with an anti-ErbB3 antibody from equal amounts of total protein, subjected to SDS-PAGE, and analyzed by Western blotting using an anti-phosphotyrosine antibody (αPY). Filters were stripped and reprobed with anti-ErbB3 antibody recognizing the intracellular region of ErbB3.

Figure 3:
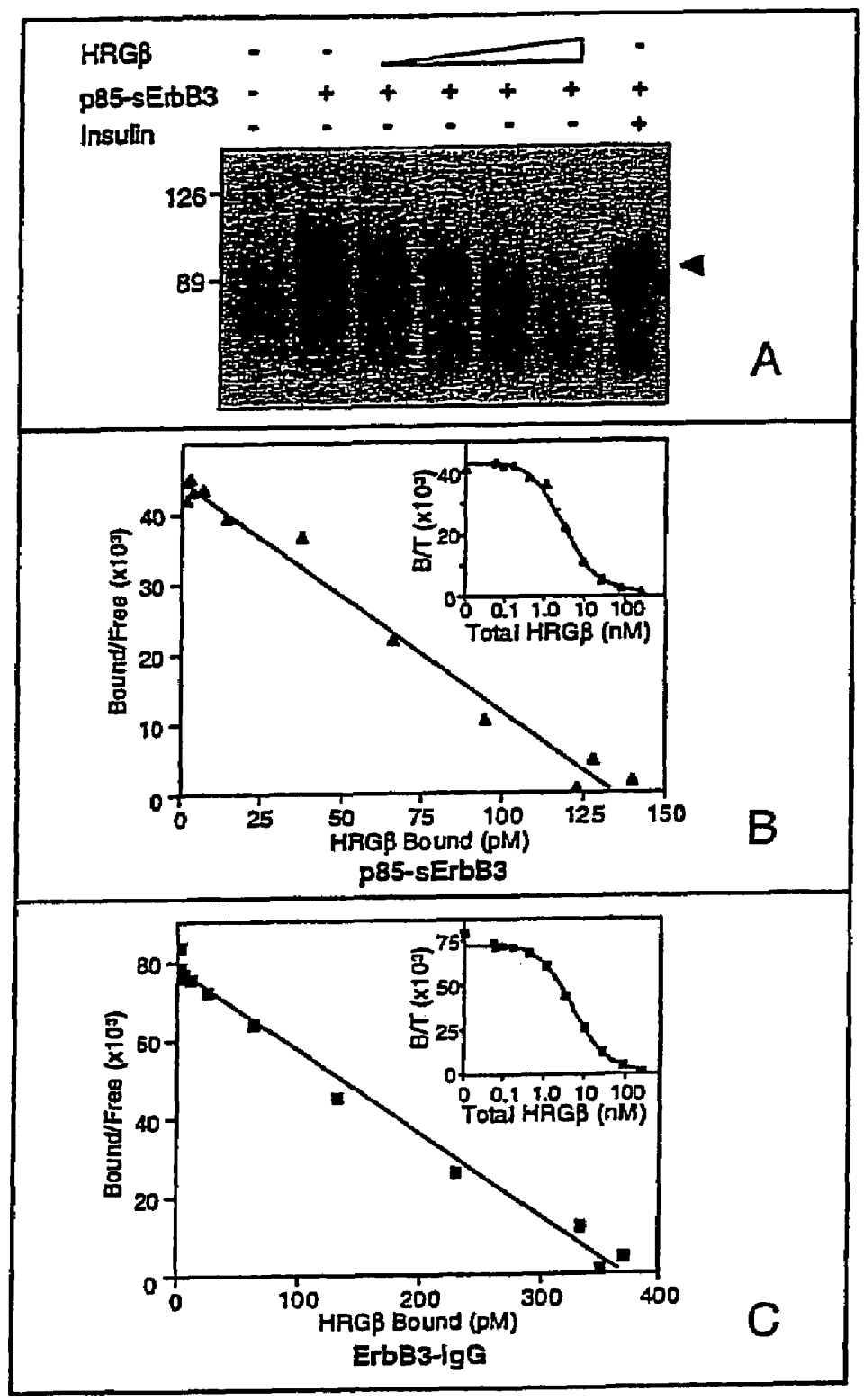

FIG. 3. p85-sErbB3 binds to HRG. (A) HRGβ was crosslinked to p85-sErbB3 (25 nM) with $BS^3$ after incubating in the presence of 50 nM $^{125}$I-HRGβ without or with increasing concentrations (0.16, 0.32, 0.64, 1.25 μM) of unlabeled HRGβ. Insulin (1.25 μM) was used as a negative control. The arrowhead indicates a 90 kDa complex of $^{125}$I-HRGβ and p85-sErbB3. (B) and (C) Binding analysis of $^{125}$I-HRG to p85-sErbB3 and ErbB3-IgG fusion protein. Binding assays were performed in a 96-well plate format as described below in more detail in the Examples. Binding results were analyzed by using Scatchard method and by plotting the displacement of $^{125}$I-HRGβ$_{177-244}$ binding by unlabeled HRGβ$_{177-244}$ (Inset).

Figure 4:
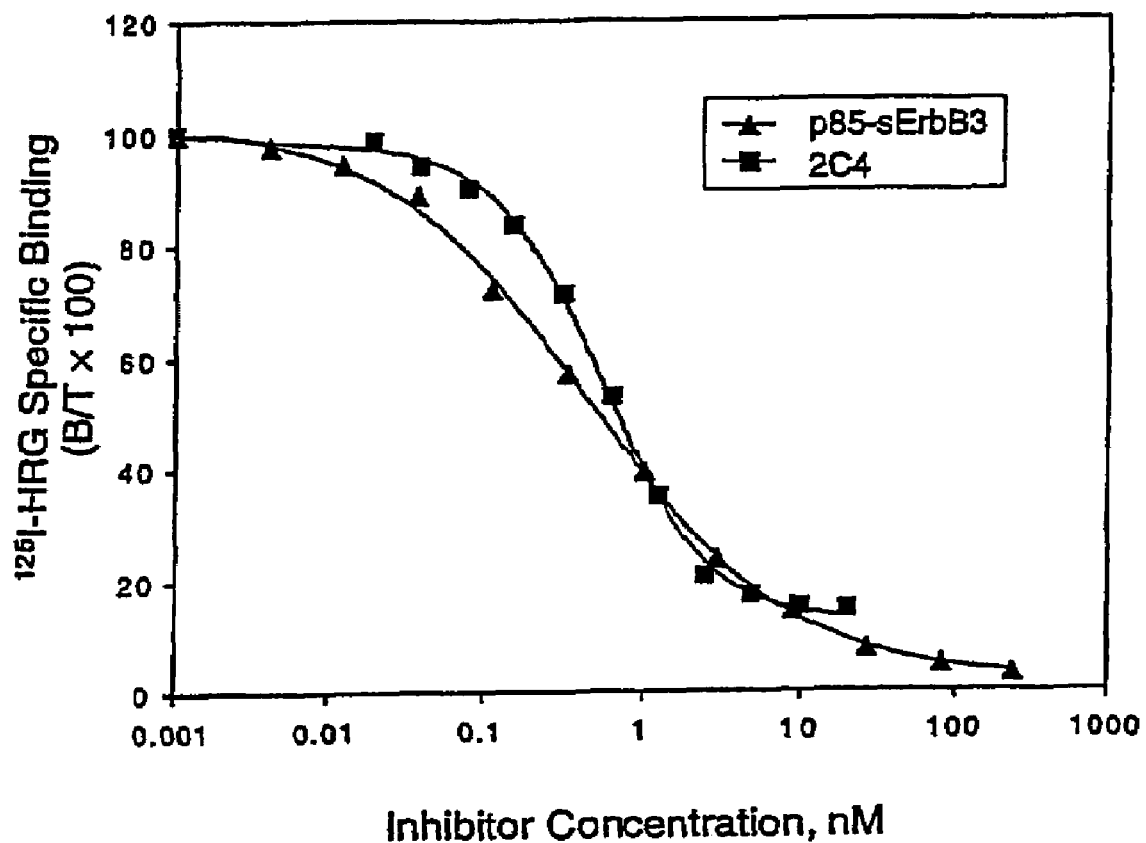

FIG. 4. Inhibition of HRGβ binding by p85-sErbB3 and by 2C4, a monoclonal antibody specific for ErbB2. T47D cells were incubated with the indicated concentrations of p85-sErbB3 and 2C4 at room temperature for 30 min. $^{125}$I-HRGβ$_{177-244}$ (0.1 nM) was then added and binding reactions were performed as described below in more detail in the Examples. $^{125}$I-HRGβ$_{177-244}$ bound to the cell surface was measured using a gamma counter.

Figure 5:
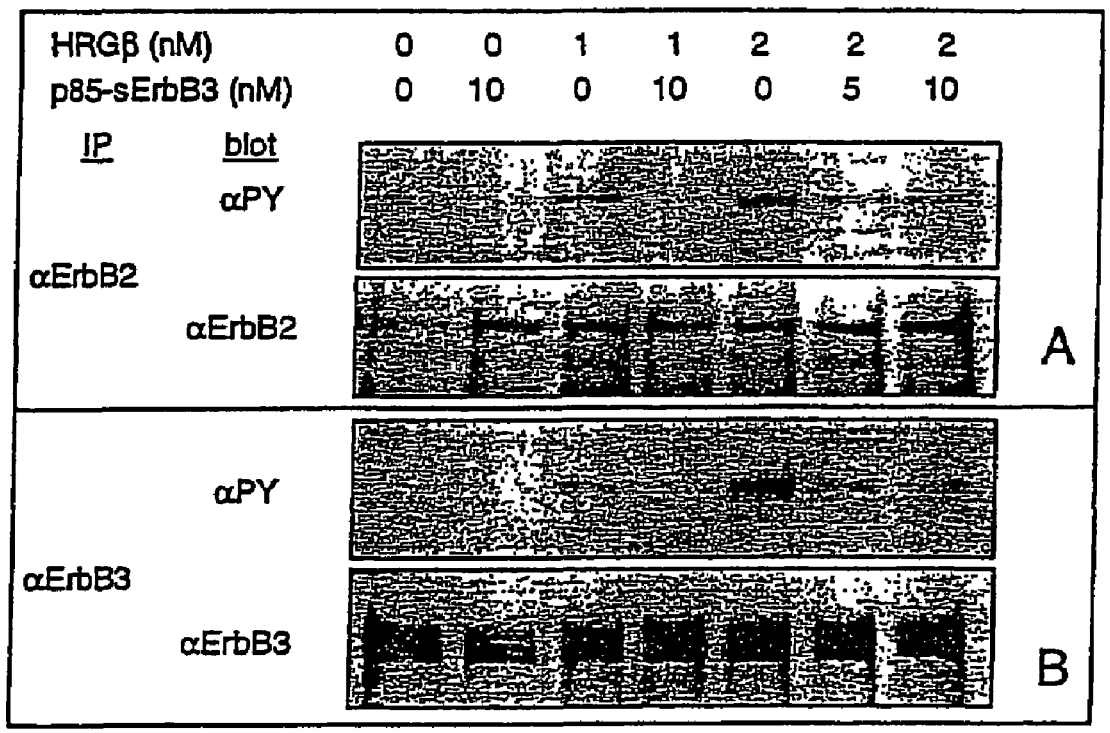

FIG. 5. p85-sErbB3 blocks HRG-induced activation of ErbB2 and ErbB3 in the Ba/F3 (ErbB2+ErbB3) cells. Cells were untreated or stimulated with HRGβ$_{1-241}$ alone or HRGβ$_{1-241}$ plus purified p85-sErbB3 for 10 min at room temperature. Receptor phosphorylation levels and ErbB2 and ErbB3 receptor levels were determined by anti-ErbB2 (A) and anti-ErbB3 (B) immunoprecipitation followed by Western blotting as described in FIG. 2.

Figure 6:
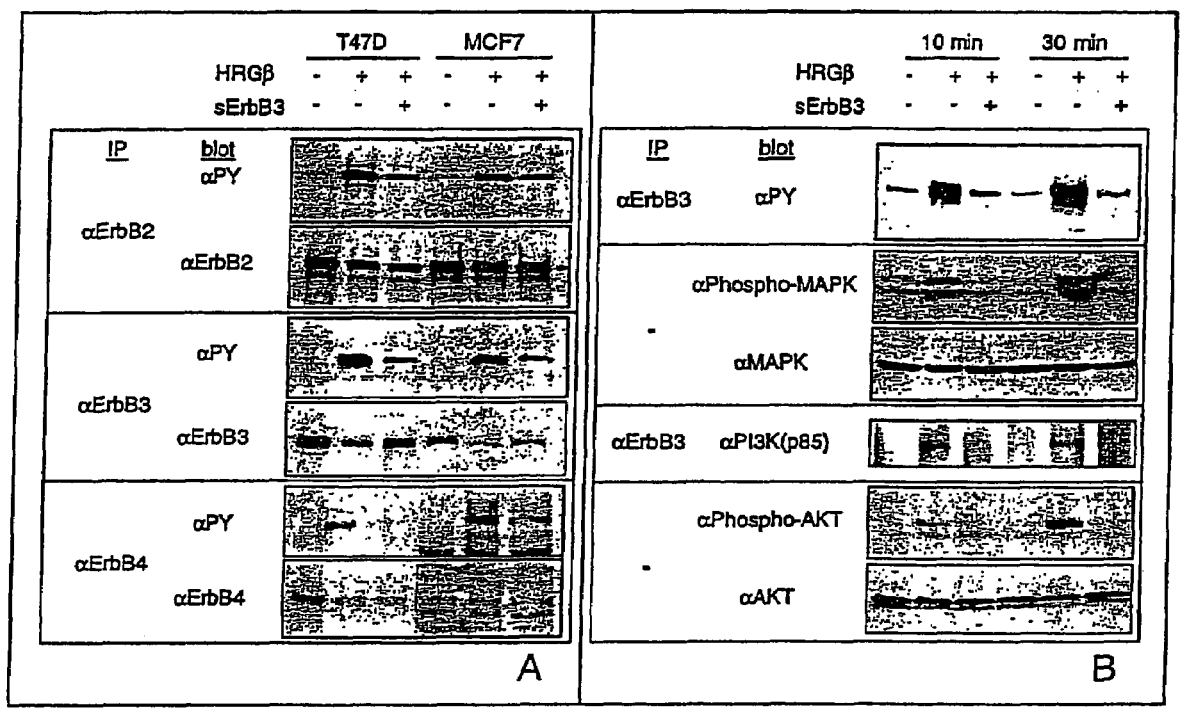

FIG. 6. p85-sErbB3 blocks HRG-induced activation of ErbB proteins and their downstream activators MAPK, PI3K (p85), and Akt. (A) p85-sErbB3 blocks HRG-induced activation of ErbB2, ErbB3, and ErbB4 in T47D and MCF7 breast carcinoma cells. Serum-starved cells were stimulated with no HRGβ, HRGβ, alone, or 6 nM HRGβ plus 36 nM p85-sErbB3 for 10 min at room temperature. Receptor phosphorylation levels and ErbB2, ErbB3, and ErbB4 receptor levels were determined by immunoprecipitation followed by Western blotting. (B) p85-sErbB3 inhibits HRG-induced association of PI3K (p85) with ErbB3 and activation of MAPK and Akt in T47D cells. Cells were treated with 1 nM HRGβ and 10 nM p85-sErbB3 for 10 min or 30 min and analyzed for activation of ErbB3. Association of PI3K (p85) with ErbB3 was analyzed by immunoprecipitation of cell lysates using an anti-ErbB3 antibody followed by Western blotting of anti-P13K (p85) antibody. Activation of MAPK and Akt was examined by Western blotting of cell lysates using antibodies specific to phospho-MAPK and phospho-Akt.

Figure 7:
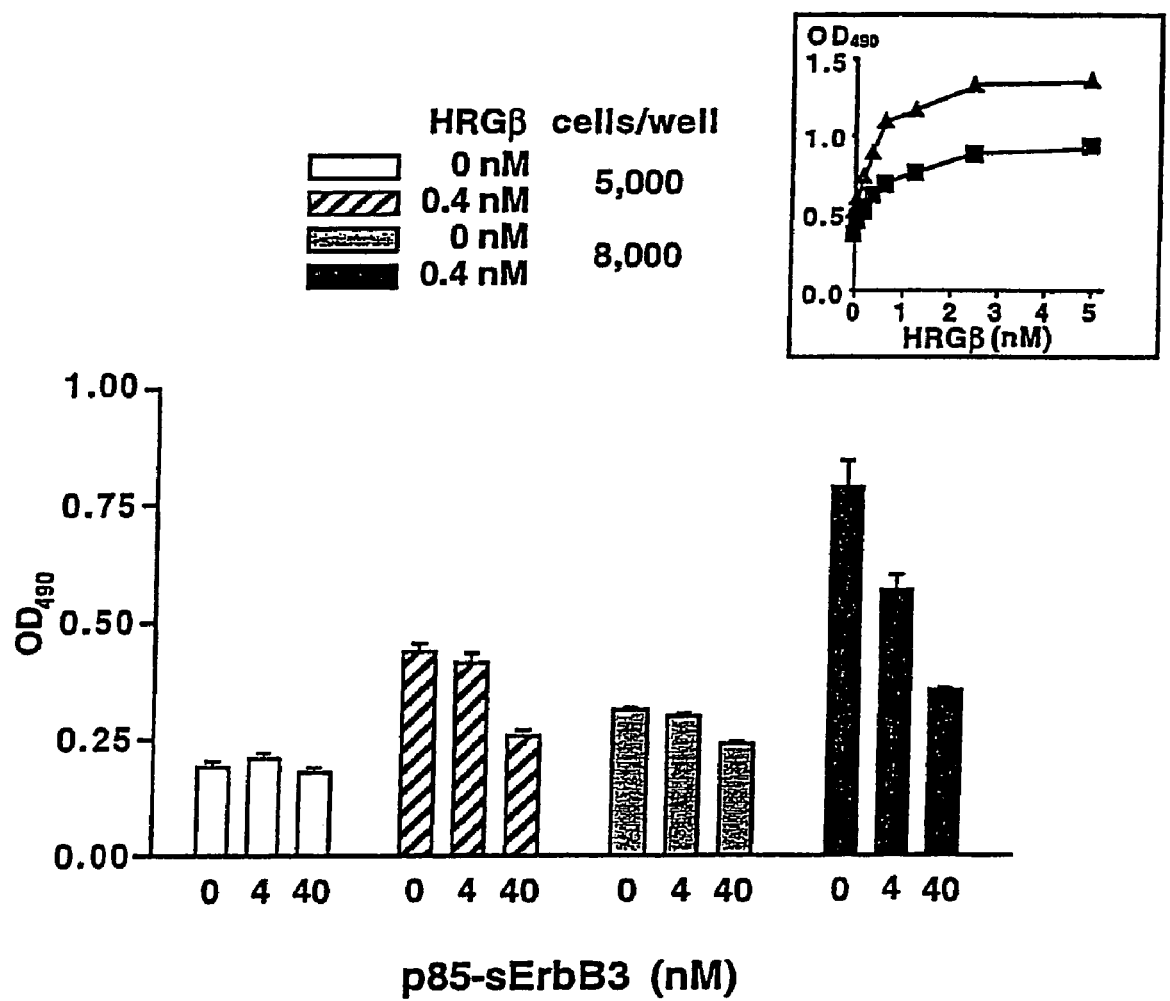

FIG. 7. p85-sErbB3 inhibits cell growth stimulation by HRG. MCF7 cells were trypsinized, washed, and plated at a density of 5,000 (squares) or 8,000 cells/well (triangles) in 96-well plates with increasing concentrations of HRGβ in serum-free medium and growth was measured after 3 days (inset). MCF7 cells were trypsinized, washed, incubated with p85-sErbB3 for 30 min, and plated with or without 0.4 nM HRGβ in serum-free medium. At 40 nM (a 100-fold molar excess to HRGβ) in the presence of HRGβ, p85-sErbB3 inhibited cell growth by 75% and 90%, at densities of 5,000 and 8,000 cells/well, respectively, whereas the same concentration of p85-sErbB3 did not affect cell growth in the absence of HRGβ. The data presented are the mean ±standard deviation of six replicates. This experiment was repeated three times and the results shown represent all three trials.

DEFINITIONS

As used herein, the term "soluble" ErbB3 (sErbB3) means that the ErbB3 polypeptide is found in a form that is not anchored to the membrane of a cell, i.e., a portion of the sErbB3 is not found physically embedded in the lipid bilayer which comprises the cell membrane in the organism of its origin. As used herein, the term "biological activity" of a peptide of the invention is defined to mean a polypeptide comprising a subunit of a peptide having SEQ ID NO:2, or a variant thereof, which has at least about 10%, preferably at least about 50%, and more preferably at least about 90% of the activity of a peptide having SEQ ID NO:2. The activity of a peptide of the invention can be measured by methods well known in the art including, but not limited to, the ability to bind heregulins, or the ability of the peptide to elicit a sequence-specific immune response when the peptide is administered to an organism, e.g., goat, sheep or mice.

The terms "recombinant nucleic acid" or "preselected nucleic acid," e.g., "recombinant DNA sequence or segment" or "preselected DNA sequence or segment" refer to a nucleic acid that has been derived or isolated from any appropriate tissue source and that may be subsequently chemically altered, typically in vitro, so that its sequence is not naturally occurring, or corresponds to naturally occurring sequences that are not positioned as they would be positioned in a genome which has not been transformed with exogenous DNA. An example of preselected DNA "derived" from a source, would be a DNA sequence that is identified as a useful fragment within a given organism and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

"Regulatory sequences" is defined to mean RNA or DNA sequences necessary for the expression, post-transcriptional modification, translation, and post-translational modification of an operably linked coding sequence in a particular host organism. The control sequences that are suitable for prokaryotic cells, for example, include a promoter, and optionally an operator sequence, and a ribosome binding site. Eukaryotic cells are known to utilize promoters, stop sequences, enhancers, splicing, and polyadenylation signal sequences, as well as glycosylation and secretory signal sequences.

As used herein, the term "cell line" or "host cell" is intended to refer to well-characterized homogenous, biologically pure populations of cells. These cells may be eukaryotic cells that are neoplastic or which have been "immortalized" in vitro by methods known in the art, as well as primary cells, or prokaryotic cells. The cell line or host cell is preferably of mammalian origin, but cell lines or host cells of non-mammalian origin may be employed, including avian, plant, insect, yeast, fungal or bacterial sources. Generally, the preselected DNA sequence is related to a DNA sequence that is resident in the genome of the host cell but is not expressed, or not highly expressed, or, alternatively, over-expressed.

The terms "transfected" or "transformed" are used herein to include any host cell or cell line, the genome of which has been altered or augmented by the presence of at least one preselected DNA sequence, which DNA is also referred to in the art of genetic engineering as "heterologous DNA," "recombinant DNA," "exogenous DNA," "genetically engineered DNA," "non-native DNA," or "foreign DNA," wherein said DNA was isolated and introduced into the genome of the host cell or cell line by the process of genetic engineering. The host cells of the present invention are typically produced by transfection with a DNA sequence in a plasmid expression vector, a viral expression vector, or as an isolated linear DNA sequence. Preferably, the transfected DNA is a chromosomally integrated recombinant DNA sequence, which comprises a gene encoding an sErbB3 isoform, which host cell may or may not express significant levels of autologous or "native" sErbB3.

DESCRIPTION OF THE INVENTION

Using various recombinant forms of EGFR, it has been shown that efficient inhibition of full-length EGFR activation by dominant-negative heterodimerization occurs only when these deletion mutants retain the transmembrane domain and the extracellular domain. Similarly, a recombinant dominant-negative ErbB3 mutant with a deleted cytoplasmic domain but which retains its transmembrane domain can inhibit full-length ErbB2 and ErbB3 activation. In contrast, in avian tissues, expression of a naturally occurring sEGFR/ErbB1 inhibits TGFα dependent transformation. An aberrant soluble EGFR secreted by the A431 human carcinoma cell line also has been reported to inhibit the kinase activity of purified full-length EGFR in a ligand-independent manner. These soluble EGFR/ErbB1 receptors do not function as antagonists through high affinity ligand-binding. Similarly, herstatin, a naturally occurring soluble ErbB2 protein which inhibits ErbB2 activation appears to function by blocking ErbB2 dimerization; this inhibition is thought to be mediated via ligand-independent binding of herstatin to ErbB2. In contrast, sErbB3, including p85-sErbB3 and p45-sErbB3, inhibits HRG-induced stimulation of ErbB2, ErbB3, and ErbB4, at least in part, by neutralizing ligand activity through competitive binding. The present invention discloses that p85-sErbB3 is capable of binding to the cell surface.

The physiological role of p85-sErbB3 in normal tissues also has not been understood to date. As discussed in greater detail below, although a much higher concentration (100-fold) was required to inhibit cell growth, a 10-fold molar excess of p85-sErbB3 was sufficient for inhibition of phosphorylation of ErbB receptors. At this ratio, a small fraction of receptors are still activated and are sufficient for growth stimulation. It is known that the 2.1 kb transcript encoding p85-sErbB3 is expressed at low levels compared to the full-length c-erbB3 transcript in all cell lines and tissues examined to date, however, local expression of this transcript has been studied in detail. It is, therefore, plausible that p85-sErbB3 acts as a HRG antagonist locally in a tissue-specific and/or stage-specific manner, and related studies to examine the distribution of p85-sErbB3 in selected tissues are currently underway. Research in the field shows that local concentrations of autocrine growth factors such as EGF are exquisitely regulated and do not travel far from the cell surface from which they are released. In this context, tightly regulated levels of local p85-sErbB3 expression have important consequences on cellular activities, such as HRG-mediated cell growth. These consequences are even more dramatic in cancer cells where cell polarity is typically lost, resulting in deregulation of normal spatial and temporal control of growth factor:receptor interactions.

The present invention provides several novel isolated and purified nucleic acids which encode isoforms of ErbB3 and nucleic acids encoding engineered variants of these proteins. Preferred embodiments are nucleic acids which specifically encode isoforms of ErbB3 whose amino acid sequence comprises the sequence of SEQ ID NO: 2 and SEQ ID NO: 4. The present invention also defines the biochemical and biological characteristics of a novel sErbB3 isoform designated p85-sErbB3. Embodiments of the present invention relate to the use of p85-sErbB3 as a unique HRG inhibitor because it can block HRG binding to cell surface receptors via binding to HRG with high affinity, thereby, inhibiting HRG-induced stimulation of ErbB2, ErbB3, and ErbB4. This inhibition is sufficient to effectively block HRG-stimulated cell growth. These novel sErbB3 receptor isoforms, therefore, are potent modulators of HRG regulated cell proliferation and differentiation in normal human tissues, and as such provide an ideal candidate for the development of novel cancer therapeutics.

EXAMPLES AND PREFERRED EMBODIMENTS

Conditioned Media from Cells Expressing p45-sErbB3 and p85-sErbB3 Inhibit HRG Activation of ErbB3. p45-sErbB3 and p85-sErbB3 are naturally occurring secreted products of the ErbB3 gene (Lee and Maihle 1998). p45-sErbB3 contains the amino-terminal 310 amino acids of ErbB3 and two unique carboxy-terminal amino acid residues. p85-sErbB3 contains the amino-terminal 519 amino acids of ErbB3 and 24 unique carboxy-terminal amino acid residues (See FIG. 1). To examine whether p45-sErbB3 and p85-sErbB3 can modulate HRG receptor activation cells stably transfected with these corresponding cDNA clones were isolated. These cells secrete p45-sErbB3 and p85-sErbB3 into the culture medium (See FIG. 2A). The conditioned medium from these cells was used as the source of p45-sErbB3 or p85-sErbB3 in a series of preliminary experiments described below.

To test the ability of p45-sErbB3 and p85-sErbB3 to modulate aspects of HRG-mediated ErbB receptor activation a clonal derivative of the Ba/F3 cell line expressing exogenous ErbB2 and ErbB3 was stimulated with HRGα EGF domain$_{177-241}$ (HRGα) and HRGβ1$_{176-246}$ (HRGβ) in the absence or presence of concentrated conditioned media containing p45-sErbB3 and p85-sErbB3. As shown in FIG. 2, HRGβ was at least 20-fold more effective than HRGα in stimulating ErbB3 tyrosine phosphorylation. Conditioned media containing sErbB3 inhibited HRGα-stimulated ErbB3 activation by 40% (p45-sErbB3) and 80% (p85-sErbB3) at 1 µg/ml HRGα, as determined by densitometric analysis. However, at a higher concentration (2 µg/ml), conditioned media containing p85-sErbB3 decreased activation by 30%, although inhibition by conditioned media containing p45-sErbB3 was negligible (See FIG. 2A). In the presence of conditioned medium containing either p45-sErbB3 or p85-sErbB3, ligand stimulation of ErbB3 tyrosine phosphorylation was decreased by 60% and 90%, respectively, at both 50 and 100 ng/ml HRGβ (See FIG. 2C). These data indicate that p85-sErbB3 inhibited ErbB3 phosphorylation in response to both HRGα and HRGβ more effectively than p45-sErbB3, although the concentration of p85-sErbB3 used in these studies was lower than that of p45-sErbB3 (FIG. 2A).

Purification of p85-sErbB3. p85-sErbB3 was isolated from a concentrated conditioned medium of cells stably transfected with a cDNA clone R31F encoding p85-sErbB3 and was purified in two steps. The first step was lectin affinity chromatography with a Con A column (Sigma). The bound p85-sErbB3 was washed with column buffer (10 mM Tris-HCl, pH 7.5, 150 mM NaCl, 1 mM MnCl$_2$, and 1 mM CaCl$_2$) and eluted using column buffer containing 1 M α-methyl D-mannoside, then dialyzed against 20 mM Tris-HCl, pH 7.5 overnight. The second step of purification was accomplished using a Mono Q®, an ion exchanger for resolution of proteins and peptides, ion exchange FPLC®, i.e., a microprocessor controlled, solvent delivery apparatus used in purification of biologically active compounds column (Pharmacia). The bound p85-sErbB3 was eluted from the column with 0-500 mM NaCl gradient containing 20 mM Tris-HCl, pH 7.5. Samples taken from each step were subjected to SDS-PAGE in duplicate and analyzed by Coomassie staining and by Western blot using anti-ErbB3 236 antibody recognizing the extracellular domain of the ErbB3 (Lee and Maihle 1998). The final p85-sErbB3 pool was homogeneous on SDS-PAGE, and the identity of the purified protein was confirmed by Western blot analysis. Purified preparations of p85-sErbB3 were used in all subsequent experiments.

p85-sErbB3 Binds to HRG with High Affinity. Previous reports based the assignment of the subdomain boundaries of the ErbB3 extracellular domain on the subdomain boundaries of EGFR (Lee and Maihle 1998) as defined by the genomic structure of avian ErbB1 (Callaghan, Antczak et al. 1993).

Accordingly, p85-sErbB3 is composed of subdomains I through III and includes the first 45 amino acids of subdomain IV (aa 1-519), and a unique twenty-four amino acid sequence at the carboxy-terminus. Binding studies using heregulins indicate that subdomains I and II are required for heregulin binding (Singer, Landgraf et al. 2001). On the other hand, for EGF binding to EGFR subdomains I and III are low and high affinity binding sites, respectively (Lax, Bellot et al. 1989). Because p85-sErbB3 contains both subdomains I through III the present invention determined that p85-sErbB3 would bind to heregulins.

Direct binding between p85-sErbB3 and radiolabeled HRGβ was examined using the chemical crosslinker $BS^3$. As shown in FIG. 3A, a protein complex of 90 kDa was formed between p85-sErbB3 and $^{125}$I-HRGβ. Formation of this complex could be inhibited by addition of excess cold HRGβ but not by addition of excess insulin, indicating that p85-sErbB3 binding to HRGβ is specific and that purified preparations of p85-sErbB3 are biologically active. An analysis of $^{125}$I-HRGβ$_{177-244}$ binding to immobilized p85-sErbB3 was then performed using an ErbB3-IgG homodimer as a positive control. As shown in FIG. 3, p85-sErbB3 binds to HRGβ$_{177-244}$ with a $K_D$ of 3.0±0.2 nM. In comparison, ErbB3-IgG binds to HRGβ$_{177-244}$ with a $K_D$ of 4.7±0.2 nM. These results demonstrate that p85-sErbB3 binds to HRGβ$_{177-244}$ with an affinity similar to that of the extracellular domain of ErbB3. Based on the results of these two complementary experimental approaches, the present invention establishes the use of p85-sErbB3 to bind to HRG with an affinity equivalent to the affinity of HRG for the full-length extracellular domain of ErbB3.

p85-sErbB3 Inhibits Binding of HRG to Receptors on the Cell Surface. The present invention also discloses the use of p85-sErbB3 to effectively limit binding of heregulin to cell surface receptors in the breast carcinoma cell line T47D. This cell line expresses all four ErbB receptors at moderate levels. Cells were incubated with varying concentrations of p85-sErbB3 in the presence of $^{125}$I-labeled HRGβ$_{177-244}$. Simultaneously, a separate group of cells was incubated with $^{125}$I-HRGβ$_{177-244}$ in the presence of varying concentrations of 2C4, a monoclonal antibody specific for the ErbB2 extracellular domain (Lewis, Lofgren et al. 1996). As shown by the inhibition curves (See FIG. 4), p85-sErbB3 and 2C4 inhibit HRGβ$_{177-244}$ binding to cell surface receptors with similar $IC_{50}$ values (0.45±0.03 nM and 0.55±0.03 nM, respectively) although the mechanism of inhibition by these two molecules is distinct. Although 2C4 inhibits heregulin binding to cell surface receptors by blocking ErbB2-ErbB3 heterodimerization via binding to the ErbB2 extracellular domain (Fitzpatrick, Pisacane et al. 1998), p85-sErbB3 inhibited receptor activation, at least in part, by competing for heregulin binding to the cell surface.

p85-sErbB3 Blocks HRG-Induced Activation of ErbB2, ErbB3, and ErbB4. The present invention also examined the ability of p85-sErbB3 to modulate HRG-stimulated receptor activation in the Ba/F3 (ErbB2+ErbB3) cell line using purified p85-sErbB3. This allowed an analysis of the mechanism of p85-sErbB3 mediated inhibition in a quantitative manner. As shown in FIG. 5, when Ba/F3 (ErbB2+ErbB3) cells were treated with p85-sErbB3 at a 10-fold molar excess over HRGβ$_{1-241}$, ErbB3 phosphorylation levels were reduced to basal levels. A similar level of receptor inhibition also was apparent when either a 2.5- or 5-fold molar excess of p85-sErbB3 was used in these experiments. Exogenous addition of p85-sErbB3 also inhibited HRG-induced ErbB2 activation. p85-sErbB3 blocked HRG stimulation whether the cells were treated with the EGF-like domain of HRG (HRGα or HRGβ), as shown in FIG. 2, or with HRGβ$_{1-241}$ (See FIG. 5), suggesting that inhibition by p85-sErbB3 occurs, at least in part, through a direct interaction between p85-sErbB3 and the EGF-like domain of HRG. Cells treated with the same concentration of p85-sErbB3 but not stimulated with HRG did not exhibit altered ErbB2 or ErbB3 tyrosine phosphorylation, or show any change in the level of either ErbB2 or ErbB3 expression, suggesting that p85-sErbB3 does not function as a "ligand" for these receptors.

To examine whether exogenous addition of p85-sErbB3 exerts the same inhibitory effect on endogenously expressed ErbB receptors, and to determine whether p85-sErbB3 could modulate other members of the EGF receptor family, the activity of p85-sErbB3 in two breast carcinoma cell lines, i.e., T47D and MCF7, was tested. As shown in FIG. 6A, addition of p85-sErbB3 (at a 6-fold molar excess relative to HRGβ) inhibited HRG-induced activation of ErbB2, ErbB3, and ErbB4 in both the T47D and MCF7 cell lines. In contrast, at least in these two cell lines which express low EGFR levels, EGFR phosphorylation remained at basal level in cells treated with HRGβ regardless of whether p85-sErbB3 was present or not. Similarly, EGF-induced phosphorylation of EGFR or ErbB2, or, to a lesser degree, phosphorylation of ErbB3, was not decreased by p85-sErbB3. These results demonstrate that inhibition by p85-sErbB3 is specific for HRG-induced activation of ErbB2, ErbB3, and ErbB4.

It is notable that in the T47D cells, a decrease in ErbB2, ErbB3, and ErbB4 protein levels following HRG stimulation was observed. In MCF7 cells a decrease in ErbB3 levels also was apparent when HRG was added to the culture medium (See FIG. 6A). It has been reported that the polyclonal ErbB3 antibody specific to the carboxy-terminal 17 aa used in this study preferentially recognizes non-phosphorylated ErbB3 on Western blots (Vartanian, Goodearl et al. 1997). Thus, when T47D or MCF7 cells are stimulated with HRG, a significant fraction of ErbB3 is phosphorylated, and, therefore, undetectable with this particular ErbB3 antibody. The anti-ErbB antibodies used in these experiments recognize the carboxy-terminal 17 aa (ErbB3) and 18 aa (ErbB2 and ErbB4) sequences of these receptors. Each of these sequences contains one tyrosine residue. Immunoblot detection by the anti-ErbB2 and ErbB4 antibodies used in this study, therefore, may reflect either the level of receptor expression or the unphosphorylated fraction of these receptors.

p85-sErbB3 Inhibits Activation of Downstream Effectors of HRG. HRG-stimulated activation of ErbB2, ErbB3, and ErbB4 leads to activation of two major signal transduction pathways: the PI3K pathway and the MAPK pathway (Wallasch, Weiss et al. 1995). The present invention tested whether p85-sErbB3 could inhibit activation of these two downstream effector pathways in T47D cells. Specifically, the present invention examined activation of MAPK and Akt by analyzing the phosphorylation levels of these proteins, and examined the ability of p85 phosphatidylinositide 3-kinase ("PI3K") to interact with ErbB3 following HRGβ treatment. In the presence of p85-sErbB3 (10-fold molar excess relative to HRGβ), tyrosine phosphorylation of ErbB3 was reduced to basal levels. In the same cell population, addition of exogenous p85-sErbB3 abrogated the phosphorylation of both MAPK and Akt as determined by Western blot analysis, and inhibited ErbB3's association with p85 PI3K (See FIG. 6B). These results further demonstrate that p85-sErbB3 can inhibit the activation of ErbB2, ErbB3, and ErbB4, and this inhibition affects the activation of downstream signaling molecules such as MAPK, Akt, and PI3K.

p85-sErbB3 Inhibits HRG-stimulated Cell Growth. The present invention also discloses the inhibition of HRG-induced phosphorylation of ErbB receptors by p85-sErbB3 as correlated with the modulation of HRG's biological effects. Specifically, a cell growth assay using MCF7 cells stimulated with HRGβ was performed and showed that, within the concentration range tested, growth of this cell line was dose-dependent (See FIG. 7). It was observed that at a concentration of 0.4 mM HRGβ the cell growth rate was half of the rate observed at saturating levels of HRGβ. In cell cultures grown in the presence of 0.4 nM HRGβ and p85-sErbB3 (a 100-fold molar excess relative to HRGβ), p85-sErbB3 inhibited cell growth by 75% and 90%, at densities of 5,000 and 8,000 cells/well, respectively, whereas the same concentration of p85-sErbB3 did not affect cell growth in the absence of HRGβ (See FIG. 7). Thus, the present invention discloses the use of p85-sErbB3 as a potent inhibitor of HRG-dependent breast carcinoma cell growth in vitro.

We claim:

1. An expression vector encoding an sErbB3, wherein said sErbB3 consists of SEQ ID NO: 6 or SEQ ID NO: 8.

2. The expression vector of claim 1, wherein the expression vector is a plasmid or a virus.

3. An isolated host cell comprising an expression vector encoding an sErbB3, wherein said sErbB3 consists of SEQ ID NO: 6 or SEQ ID NO: 8.

4. The isolated host cell of claim 3, wherein the cell is a prokaryote or a eukaryote.

5. A method of producing an sErbB3 comprising the steps of:
   a. culturing an isolated host cell comprising an expression vector encoding an sErbB3, wherein said sErbB3 consists of SEQ ID NO: 6 or SEQ ID NO: 8; and
   b. harvesting said sErbB3.

6. An isolated nucleic acid sequence selected from the group consisting of:
   a. a nucleic acid sequence consisting of SEQ ID NO: 5 or SEQ ID NO: 7;
   b. a nucleic acid sequence encoding a protein consisting of SEQ ID NO: 6 or SEQ ID NO: 8; and
   c. a nucleic acid sequence complementary to the nucleic acid sequence a) or b).

7. An isolated nucleic acid sequence consisting of SEQ ID NO: 5 or SEQ ID NO: 7.

8. An isolated nucleic acid sequence encoding a protein consisting of SEQ ID NO: 6 or SEQ ID NO: 8.

9. An isolated nucleic acid sequence which is at least 99% identical to SEQ ID NO: 5 or SEQ ID NO: 7.

10. An isolated amino acid sequence consisting of SEQ ID NO: 6 or SEQ ID NO: 8.

* * * * *

SEQUENCE LISTING

```
<160> NUMBER OF SEQ ID NOS: 8

<210> SEQ ID NO 1
<211> LENGTH: 1800
<212> TYPE: DNA
<213> ORGANISM: Homo sapiens
<220> FEATURE:
<221> NAME/KEY: CDS
<222> LOCATION: (61)..(1746)

<400> SEQUENCE: 1
cgggcccccc ctcgaggtcg ggccggactt ggctgggctc ccttcaccct ctgcggagtc      60 atg agg gcg aac gac gct ctg cag gtg ctg ggc ttg ctt ttc agc ctg     108
Met Arg Ala Asn Asp Ala Leu Gln Val Leu Gly Leu Leu Phe Ser Leu
1               5                   10                  15 gcc cgg ggc tcc gag gtg ggc aac tct cag gca gtg tgt cct ggg act     156
Ala Arg Gly Ser Glu Val Gly Asn Ser Gln Ala Val Cys Pro Gly Thr
            20                  25                  30 ctg aat ggc ctg agt gtg acc ggc gat gct gag aac caa tac cag aca     204
Leu Asn Gly Leu Ser Val Thr Gly Asp Ala Glu Asn Gln Tyr Gln Thr
        35                  40                  45 ctg tac aag ctc tac gag agg tgt gag gtg gtg atg ggg aac ctt gag     252
Leu Tyr Lys Leu Tyr Glu Arg Cys Glu Val Val Met Gly Asn Leu Glu
    50                  55                  60 att gtg ctc acg gga cac aat gcc gac ctc tcc ttc ctg cag tgg att     300
Ile Val Leu Thr Gly His Asn Ala Asp Leu Ser Phe Leu Gln Trp Ile
65                  70                  75                  80 cga gaa gtg aca ggc tat gtc ctc gtg gcc atg aat gaa ttc tct act     348
Arg Glu Val Thr Gly Tyr Val Leu Val Ala Met Asn Glu Phe Ser Thr
                85                  90                  95 cta cca ttg ccc aac ctc cgc gtg gtg cga ggg acc cag gtc tac gat     396
Leu Pro Leu Pro Asn Leu Arg Val Val Arg Gly Thr Gln Val Tyr Asp
            100                 105                 110 ggg aag ttt gcc atc ttc gtc atg ttg aac tat aac acc aac tcc agc     444
Gly Lys Phe Ala Ile Phe Val Met Leu Asn Tyr Asn Thr Asn Ser Ser
        115                 120                 125 cac gct ctg cgc cag ctc cgc ttg act cag ctc acc gag att ctg tca     492
His Ala Leu Arg Gln Leu Arg Leu Thr Gln Leu Thr Glu Ile Leu Ser
    130                 135                 140 ggg ggt gtt tat att gag aag aac gat aag ctt tgt cac atg gac aca     540
Gly Gly Val Tyr Ile Glu Lys Asn Asp Lys Leu Cys His Met Asp Thr
145                 150                 155                 160 att gac tgg agg gac atc gtg agg gac cga gat gct gag ata gtg gtg     588
Ile Asp Trp Arg Asp Ile Val Arg Asp Arg Asp Ala Glu Ile Val Val
                165                 170                 175 aag gac aat ggc aga agc tgt ccc ccc tgt cat gag gtt tgc aag ggg     636
Lys Asp Asn Gly Arg Ser Cys Pro Pro Cys His Glu Val Cys Lys Gly
            180                 185                 190 cga tgc tgg ggt cct gga tca gaa gac tgc cag aca ttg acc aag acc     684
Arg Cys Trp Gly Pro Gly Ser Glu Asp Cys Gln Thr Leu Thr Lys Thr
        195                 200                 205
```

-continued

| | | |
|---|---|---|
| atc tgt gct cct cag tgt aat ggt cac tgc ttt ggg ccc aac ccc aac<br>Ile Cys Ala Pro Gln Cys Asn Gly His Cys Phe Gly Pro Asn Pro Asn<br>210                                215                            220 | 732 |
| cag tgc tgc cat gat gag tgt gcc ggg ggc tgc tca ggc cct cag gac<br>Gln Cys Cys His Asp Glu Cys Ala Gly Gly Cys Ser Gly Pro Gln Asp<br>225                              230                          235                  240 | 780 |
| aca gac tgc ttt gcc tgc cgg cac ttc aat gac agt gga gcc tgt gta<br>Thr Asp Cys Phe Ala Cys Arg His Phe Asn Asp Ser Gly Ala Cys Val<br>                        245                          250                          255 | 828 |
| cct cgc tgt cca cag cct ctt gtc tac aac aag cta act ttc cag ctg<br>Pro Arg Cys Pro Gln Pro Leu Val Tyr Asn Lys Leu Thr Phe Gln Leu<br>                260                          265                          270 | 876 |
| gaa ccc aat ccc cac acc aag tat cag tat gga gga gtt tgt gta gcc<br>Glu Pro Asn Pro His Thr Lys Tyr Gln Tyr Gly Gly Val Cys Val Ala<br>            275                          280                          285 | 924 |
| agc tgt ccc cat aac ttt gtg gtg gat caa aca tcc tgt gtc agg gcc<br>Ser Cys Pro His Asn Phe Val Val Asp Gln Thr Ser Cys Val Arg Ala<br>290                                295                            300 | 972 |
| tgt cct cct gac aag atg gaa gta gat aaa aat ggg ctc aag atg tgt<br>Cys Pro Pro Asp Lys Met Glu Val Asp Lys Asn Gly Leu Lys Met Cys<br>305                                310                          315                  320 | 1020 |
| gag cct tgt ggg gga cta tgt ccc aaa gcc tgt gag gga aca ggc tct<br>Glu Pro Cys Gly Gly Leu Cys Pro Lys Ala Cys Glu Gly Thr Gly Ser<br>                        325                          330                          335 | 1068 |
| ggg agc cgc ttc cag act gtg gac tcg agc aac att gat gga ttt gtg<br>Gly Ser Arg Phe Gln Thr Val Asp Ser Ser Asn Ile Asp Gly Phe Val<br>                340                          345                          350 | 1116 |
| aac tgc acc aag atc ctg ggc aac ctg gac ttt ctg atc acc ggc ctc<br>Asn Cys Thr Lys Ile Leu Gly Asn Leu Asp Phe Leu Ile Thr Gly Leu<br>                        355                          360                          365 | 1164 |
| aat gga gac ccc tgg cac aag atc cct gcc ctg gac cca gag aag ctc<br>Asn Gly Asp Pro Trp His Lys Ile Pro Ala Leu Asp Pro Glu Lys Leu<br>370                                375                            380 | 1212 |
| aat gtc ttc cgg aca gta cgg gag atc aca ggt tac ctg aac atc cag<br>Asn Val Phe Arg Thr Val Arg Glu Ile Thr Gly Tyr Leu Asn Ile Gln<br>385                                390                          395                  400 | 1260 |
| tcc tgg ccg ccc cac atg cac aac ttc agt gtt ttt tcc aat ttg aca<br>Ser Trp Pro Pro His Met His Asn Phe Ser Val Phe Ser Asn Leu Thr<br>                        405                          410                          415 | 1308 |
| acc att gga ggc aga agc ctc tac aac cgg ggc ttc tca ttg ttg atc<br>Thr Ile Gly Gly Arg Ser Leu Tyr Asn Arg Gly Phe Ser Leu Leu Ile<br>                420                          425                          430 | 1356 |
| atg aag aac ttg aat gtc aca tct ctg ggc ttc cga tcc ctg aag gaa<br>Met Lys Asn Leu Asn Val Thr Ser Leu Gly Phe Arg Ser Leu Lys Glu<br>                        435                          440                          445 | 1404 |
| att agt gct ggg cgt atc tat ata agt gcc aat agg cag ctc tgc tac<br>Ile Ser Ala Gly Arg Ile Tyr Ile Ser Ala Asn Arg Gln Leu Cys Tyr<br>450                                455                            460 | 1452 |
| cac cac tct ttg aac tgg acc aag gtg ctt cgg ggg cct acg gaa gag<br>His His Ser Leu Asn Trp Thr Lys Val Leu Arg Gly Pro Thr Glu Glu<br>465                                470                          475                  480 | 1500 |
| cga cta gac atc aag cat aat cgg ccg cgc aga gac tgc gtg gca gag<br>Arg Leu Asp Ile Lys His Asn Arg Pro Arg Arg Asp Cys Val Ala Glu<br>                        485                          490                          495 | 1548 |
| ggc aaa gtg tgt gac cca ctg tgc tcc tct ggg gga tgc tgg ggc cca<br>Gly Lys Val Cys Asp Pro Leu Cys Ser Ser Gly Gly Cys Trp Gly Pro<br>                        500                          505                          510 | 1596 |
| ggc cct ggt cag tgc ttg tcc tgt cga aat tat agc cga gga ggt gtc<br>Gly Pro Gly Gln Cys Leu Ser Cys Arg Asn Tyr Ser Arg Gly Gly Val<br>                515                          520                          525 | 1644 |

```
tgt gtg acc cac tgc aac ttt ttg aat ggg tac agt aag ggg agc cag    1692
Cys Val Thr His Cys Asn Phe Leu Asn Gly Tyr Ser Lys Gly Ser Gln
    530                 535                 540 tca agg atg ggt ggg ggt ggg gcc ctg caa tgg aac tgt tca ggt ggc    1740
Ser Arg Met Gly Gly Gly Gly Ala Leu Gln Trp Asn Cys Ser Gly Gly
545                 550                 555                 560 ata caa taaaagtctt tagacaaaaa aaaaaaaaaa aaaaaaaaaa aaaaaaaaaa     1796
Ile Gln aaaa                                                                1800

<210> SEQ ID NO 2
<211> LENGTH: 562
<212> TYPE: PRT
<213> ORGANISM: Homo sapiens

<400> SEQUENCE: 2

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
    290                 295                 300
```

-continued

```
Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
            325                 330                 335

Gly Ser Arg Phe Gln Thr Val Asp Ser Ser Asn Ile Gly Phe Val
        340                 345                 350

Asn Cys Thr Lys Ile Leu Gly Asn Leu Asp Phe Leu Ile Thr Gly Leu
        355                 360                 365

Asn Gly Asp Pro Trp His Lys Ile Pro Ala Leu Asp Pro Glu Lys Leu
    370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                405                 410                 415

Thr Ile Gly Gly Arg Ser Leu Tyr Asn Arg Gly Phe Ser Leu Leu Ile
            420                 425                 430

Met Lys Asn Leu Asn Val Thr Ser Leu Gly Phe Arg Ser Leu Lys Glu
        435                 440                 445

Ile Ser Ala Gly Arg Ile Tyr Ile Ser Ala Asn Arg Gln Leu Cys Tyr
    450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Val Ala Glu
                485                 490                 495

Gly Lys Val Cys Asp Pro Leu Cys Ser Ser Gly Gly Cys Trp Gly Pro
            500                 505                 510

Gly Pro Gly Gln Cys Leu Ser Cys Arg Asn Tyr Ser Arg Gly Gly Val
        515                 520                 525

Cys Val Thr His Cys Asn Phe Leu Asn Gly Tyr Ser Lys Gly Ser Gln
    530                 535                 540

Ser Arg Met Gly Gly Gly Ala Leu Gln Trp Asn Cys Ser Gly Gly
545                 550                 555                 560

Ile Gln

<210> SEQ ID NO 3
<211> LENGTH: 1420
<212> TYPE: DNA
<213> ORGANISM: Homo sapiens
<220> FEATURE:
<221> NAME/KEY: CDS
<222> LOCATION: (61)..(1053)

<400> SEQUENCE: 3 cgggccccccc ctcgaggtcg ggccggactt ggctgggctc ccttcaccct ctgcggagtc    60 atg agg gcg aac gac gct ctg cag gtg ctg ggc ttg ctt ttc agc ctg     108
Met Arg Ala Asn Asp Ala Leu Gln Val Leu Gly Leu Leu Phe Ser Leu
1               5                   10                  15 gcc cgg ggc tcc gag gtg ggc aac tct cag gca gtg tgt cct ggg act     156
Ala Arg Gly Ser Glu Val Gly Asn Ser Gln Ala Val Cys Pro Gly Thr
            20                  25                  30 ctg aat ggc ctg agt gtg acc ggc gat gct gag aac caa tac cag aca     204
Leu Asn Gly Leu Ser Val Thr Gly Asp Ala Glu Asn Gln Tyr Gln Thr
        35                  40                  45 ctg tac aag ctc tac gag agg tgt gag gtg gtg atg ggg aac ctt gag     252
Leu Tyr Lys Leu Tyr Glu Arg Cys Glu Val Val Met Gly Asn Leu Glu
    50                  55                  60
```

```
att gtg ctc acg gga cac aat gcc gac ctc tcc ttc ctg cag tgg att      300
Ile Val Leu Thr Gly His Asn Ala Asp Leu Ser Phe Leu Gln Trp Ile
 65             70                  75                  80 cga gaa gtg aca ggc tat gtc ctc gtg gcc atg aat gaa ttc tct act      348
Arg Glu Val Thr Gly Tyr Val Leu Val Ala Met Asn Glu Phe Ser Thr
             85                  90                  95 cta cca ttg ccc aac ctc cgc gtg gtg cga ggg acc cag gtc tac gat      396
Leu Pro Leu Pro Asn Leu Arg Val Val Arg Gly Thr Gln Val Tyr Asp
            100                 105                 110 ggg aag ttt gcc atc ttc gtc atg ttg aac tat aac acc aac tcc agc      444
Gly Lys Phe Ala Ile Phe Val Met Leu Asn Tyr Asn Thr Asn Ser Ser
        115                 120                 125 cac gct ctg cgc cag ctc cgc ttg act cag ctc acc gag att ctg tca      492
His Ala Leu Arg Gln Leu Arg Leu Thr Gln Leu Thr Glu Ile Leu Ser
    130                 135                 140 ggg ggt gtt tat att gag aag aac gat aag ctt tgt cac atg gac aca      540
Gly Gly Val Tyr Ile Glu Lys Asn Asp Lys Leu Cys His Met Asp Thr
145                 150                 155                 160 att gac tgg agg gac atc gtg agg gac cga gat gct gag ata gtg gtg      588
Ile Asp Trp Arg Asp Ile Val Arg Asp Arg Asp Ala Glu Ile Val Val
                165                 170                 175 aag gac aat ggc aga agc tgt ccc ccc tgt cat gag gtt tgc aag ggg      636
Lys Asp Asn Gly Arg Ser Cys Pro Pro Cys His Glu Val Cys Lys Gly
            180                 185                 190 cga tgc tgg ggt cct gga tca gaa gac tgc cag aca ttg acc aag acc      684
Arg Cys Trp Gly Pro Gly Ser Glu Asp Cys Gln Thr Leu Thr Lys Thr
        195                 200                 205 atc tgt gct cct cag tgt aat ggt cac tgc ttt ggg ccc aac ccc aac      732
Ile Cys Ala Pro Gln Cys Asn Gly His Cys Phe Gly Pro Asn Pro Asn
    210                 215                 220 cag tgc tgc cat gat gag tgt gcc ggg ggc tgc tca ggc cct cag gac      780
Gln Cys Cys His Asp Glu Cys Ala Gly Gly Cys Ser Gly Pro Gln Asp
225                 230                 235                 240 aca gac tgc ttt gcc tgc cgg cac ttc aat gac agt gga gcc tgt gta      828
Thr Asp Cys Phe Ala Cys Arg His Phe Asn Asp Ser Gly Ala Cys Val
                245                 250                 255 cct cgc tgt cca cag cct ctt gtc tac aac aag cta act ttc cag ctg      876
Pro Arg Cys Pro Gln Pro Leu Val Tyr Asn Lys Leu Thr Phe Gln Leu
            260                 265                 270 gaa ccc aat ccc cac acc aag tat cag tat gga gga gtt tgt gta gcc      924
Glu Pro Asn Pro His Thr Lys Tyr Gln Tyr Gly Gly Val Cys Val Ala
        275                 280                 285 agc tgt ccc cat aac ttt gtg gtg gat caa aca tcc tgt gtc agg gcc      972
Ser Cys Pro His Asn Phe Val Val Asp Gln Thr Ser Cys Val Arg Ala
    290                 295                 300 tgt cct cct gac aag atg gaa gta gat aaa aat ggg ctc aag atg tgt     1020
Cys Pro Pro Asp Lys Met Glu Val Asp Lys Asn Gly Leu Lys Met Cys
305                 310                 315                 320 gag cct tgt ggg gga cta tgt ccc aaa ggt ggg taggagatgg taagaagttg    1073
Glu Pro Cys Gly Gly Leu Cys Pro Lys Gly Gly
                325                 330 taaagagaca gcctttcctc tgagcctgcg cagaccaccc ccactgaacc tctcttacat    1133
ttgcagcctg tgagggaaca ggctctggga gccgcttcca gactgtggac tcgagcaaca    1193
ttgatggatt tgtgaactgc accaagatcc tgggcaacct ggactttctg atcaccggcc    1253
tcaatgggtt agagatcctg ccttccctcc ttagacccca gcccacgcac ccctcacagt    1313
tcatttcatt ggccaaaact ttcctatgtg gagctgacta ggaatcaaag tcataaaatt    1373
ctagcctgtt acaaaggaaa aaaaaaaaaa aaaaaaaaa aaaaaaa                    1420
```

<210> SEQ ID NO 4
<211> LENGTH: 331
<212> TYPE: PRT
<213> ORGANISM: Homo sapiens

<400> SEQUENCE: 4

Met Arg Ala Asn Asp Ala Leu Gln Val Leu Gly Leu Leu Phe Ser Leu
 1               5                  10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
    290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Gly Gly
                325                 330

<210> SEQ ID NO 5
<211> LENGTH: 2005
<212> TYPE: DNA
<213> ORGANISM: Homo sapiens
<220> FEATURE:
<221> NAME/KEY: CDS
<222> LOCATION: (61)..(1662)

<400> SEQUENCE: 5

```
cgggccccc ctcgaggtcg ggccggactt ggctgggctc ccttcaccct ctgcggagtc    60 atg agg gcg aac gac gct ctg cag gtg ctg ggc ttg ctt ttc agc ctg   108
Met Arg Ala Asn Asp Ala Leu Gln Val Leu Gly Leu Leu Phe Ser Leu
 1               5                  10                  15 gcc cgg ggc tcc gag gtg ggc aac tct cag gca gtg tgt cct ggg act   156
Ala Arg Gly Ser Glu Val Gly Asn Ser Gln Ala Val Cys Pro Gly Thr
             20                  25                  30 ctg aat ggc ctg agt gtg acc ggc gat gct gag aac caa tac cag aca   204
Leu Asn Gly Leu Ser Val Thr Gly Asp Ala Glu Asn Gln Tyr Gln Thr
         35                  40                  45 ctg tac aag ctc tac gag agg tgt gag gtg gtg atg ggg aac ctt gag   252
Leu Tyr Lys Leu Tyr Glu Arg Cys Glu Val Val Met Gly Asn Leu Glu
     50                  55                  60 att gtg ctc acg gga cac aat gcc gac ctc tcc ttc ctg cag tgg att   300
Ile Val Leu Thr Gly His Asn Ala Asp Leu Ser Phe Leu Gln Trp Ile
 65                  70                  75                  80 cga gaa gtg aca ggc tat gtc ctc gtg gcc atg aat gaa ttc tct act   348
Arg Glu Val Thr Gly Tyr Val Leu Val Ala Met Asn Glu Phe Ser Thr
                 85                  90                  95 cta cca ttg ccc aac ctc cgc gtg gtg cga ggg acc cag gtc tac gat   396
Leu Pro Leu Pro Asn Leu Arg Val Val Arg Gly Thr Gln Val Tyr Asp
            100                 105                 110 ggg aag ttt gcc atc ttc gtc atg ttg aac tat aac acc aac tcc agc   444
Gly Lys Phe Ala Ile Phe Val Met Leu Asn Tyr Asn Thr Asn Ser Ser
        115                 120                 125 cac gct ctg cgc cag ctc cgc ttg act cag ctc acc gag att ctg tca   492
His Ala Leu Arg Gln Leu Arg Leu Thr Gln Leu Thr Glu Ile Leu Ser
    130                 135                 140 ggg ggt gtt tat att gag aag aac gat aag ctt tgt cac atg gac aca   540
Gly Gly Val Tyr Ile Glu Lys Asn Asp Lys Leu Cys His Met Asp Thr
145                 150                 155                 160 att gac tgg agg gac atc gtg agg gac cga gat gct gag ata gtg gtg   588
Ile Asp Trp Arg Asp Ile Val Arg Asp Arg Asp Ala Glu Ile Val Val
                165                 170                 175 aag gac aat ggc aga agc tgt ccc ccc tgt cat gag gtt tgc aag ggg   636
Lys Asp Asn Gly Arg Ser Cys Pro Pro Cys His Glu Val Cys Lys Gly
            180                 185                 190 cga tgc tgg ggt cct gga tca gaa gac tgc cag aca ttg acc aag acc   684
Arg Cys Trp Gly Pro Gly Ser Glu Asp Cys Gln Thr Leu Thr Lys Thr
        195                 200                 205 atc tgt gct cct cag tgt aat ggt cac tgc ttt ggg ccc aac ccc aac   732
Ile Cys Ala Pro Gln Cys Asn Gly His Cys Phe Gly Pro Asn Pro Asn
    210                 215                 220 cag tgc tgc cat gat gag tgt gcc ggg ggc tgc tca ggc cct cag gac   780
Gln Cys Cys His Asp Glu Cys Ala Gly Gly Cys Ser Gly Pro Gln Asp
225                 230                 235                 240 aca gac tgc ttt gcc tgc cgg cac ttc aat gac agt gga gcc tgt gta   828
Thr Asp Cys Phe Ala Cys Arg His Phe Asn Asp Ser Gly Ala Cys Val
                245                 250                 255 cct cgc tgt cca cag cct ctt gtc tac aac aag cta act ttc cag ctg   876
Pro Arg Cys Pro Gln Pro Leu Val Tyr Asn Lys Leu Thr Phe Gln Leu
            260                 265                 270 gaa ccc aat ccc cac acc aag tat cag tat gga gga gtt tgt gta gcc   924
Glu Pro Asn Pro His Thr Lys Tyr Gln Tyr Gly Gly Val Cys Val Ala
        275                 280                 285 agc tgt ccc cat aac ttt gtg gtg gat caa aca tcc tgt gtc agg gcc   972
Ser Cys Pro His Asn Phe Val Val Asp Gln Thr Ser Cys Val Arg Ala
    290                 295                 300
```

```
tgt cct cct gac aag atg gaa gta gat aaa aat ggg ctc aag atg tgt    1020
Cys Pro Pro Asp Lys Met Glu Val Asp Lys Asn Gly Leu Lys Met Cys
305             310                 315                 320 gag cct tgt ggg gga cta tgt ccc aaa gcc tgt gag gga aca ggc tct    1068
Glu Pro Cys Gly Gly Leu Cys Pro Lys Ala Cys Glu Gly Thr Gly Ser
            325                 330                 335 ggg agc cgc ttc cag act gtg gac tcg agc aac att gat gga ttt gtg    1116
Gly Ser Arg Phe Gln Thr Val Asp Ser Ser Asn Ile Asp Gly Phe Val
        340                 345                 350 aac tgc acc aag atc ctg ggc aac ctg gac ttt ctg atc acc ggc ctc    1164
Asn Cys Thr Lys Ile Leu Gly Asn Leu Asp Phe Leu Ile Thr Gly Leu
    355                 360                 365 aat gga gac ccc tgg cac aag atc cct gcc ctg gac cca gag aag ctc    1212
Asn Gly Asp Pro Trp His Lys Ile Pro Ala Leu Asp Pro Glu Lys Leu
370                 375                 380 aat gtc ttc cgg aca gta cgg gag atc aca ggt tac ctg aac atc cag    1260
Asn Val Phe Arg Thr Val Arg Glu Ile Thr Gly Tyr Leu Asn Ile Gln
385                 390                 395                 400 tcc tgg ccg ccc cac atg cac aac ttc agt gtt ttt tcc aat ttg aca    1308
Ser Trp Pro Pro His Met His Asn Phe Ser Val Phe Ser Asn Leu Thr
                405                 410                 415 acc att gga ggc aga agc ctc tac aac cgg ggc ttc tca ttg ttg atc    1356
Thr Ile Gly Gly Arg Ser Leu Tyr Asn Arg Gly Phe Ser Leu Leu Ile
            420                 425                 430 atg aag aac ttg aat gtc aca tct ctg ggc ttc cga tcc ctg aag gaa    1404
Met Lys Asn Leu Asn Val Thr Ser Leu Gly Phe Arg Ser Leu Lys Glu
        435                 440                 445 att agt gct ggg cgt atc tat ata agt gcc aat agg cag ctc tgc tac    1452
Ile Ser Ala Gly Arg Ile Tyr Ile Ser Ala Asn Arg Gln Leu Cys Tyr
    450                 455                 460 cac cac tct ttg aac tgg acc aag gtg ctt cgg ggg cct acg gaa gag    1500
His His Ser Leu Asn Trp Thr Lys Val Leu Arg Gly Pro Thr Glu Glu
465                 470                 475                 480 cga cta gac atc aag cat aat cgg ccg cgc aga gac tgc ggt gag gga    1548
Arg Leu Asp Ile Lys His Asn Arg Pro Arg Arg Asp Cys Gly Glu Gly
                485                 490                 495 aag ggt ctg cta ggt ggt gag aat agg gag tca ggg agg aga ggg ctg    1596
Lys Gly Leu Leu Gly Gly Glu Asn Arg Glu Ser Gly Arg Arg Gly Leu
            500                 505                 510 aaa gga cta ttc tgc cct aga cgt ggg agt agg gtt gag gga tgg aac    1644
Lys Gly Leu Phe Cys Pro Arg Arg Gly Ser Arg Val Glu Gly Trp Asn
        515                 520                 525 caa gga gaa ggg ggc tgt taggctggaa gcagtaacga ggaagaataa           1692
Gln Gly Glu Gly Gly Cys
    530 tgaagagagg gcttgctggg agtcctcaga ctcctctcct aacccacccc ttcctttcca  1752 gtggcagagg gcaaagtgtg tgacccactg tgctcctctg ggggatgctg ggcccaggc   1812 cctggtcagt gcttgtcctg tcgaaattat agccgaggag gtgtctgtgt gacccactgc  1872 aactttctga atgggtacag taaggggagc cagtcaagga tgggtggggg tggggccctg  1932 caatggaact gttcaggtgg catacaataa aagtctttag acagcaaaaa aaaaaaaaa   1992 aaaaaaaaaa aaa                                                     2005

<210> SEQ ID NO 6
<211> LENGTH: 534
<212> TYPE: PRT
<213> ORGANISM: Homo sapiens
```

<400> SEQUENCE: 6

```
Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
    290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
        355                 360                 365

Asn Gly Asp Pro Trp His Lys Ile Pro Ala Leu Asp Pro Glu Lys Leu
    370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                405                 410                 415
```

```
       Thr Ile Gly Gly Arg Ser Leu Tyr Asn Arg Gly Phe Ser Leu Leu Ile
                       420                 425                 430

Met Lys Asn Leu Asn Val Thr Ser Leu Gly Phe Arg Ser Leu Lys Glu
                   435                 440                 445

Ile Ser Ala Gly Arg Ile Tyr Ile Ser Ala Asn Arg Gln Leu Cys Tyr
               450                 455                 460

His His Ser Leu Asn Trp Thr Lys Val Leu Arg Gly Pro Thr Glu Glu
       465                 470                 475                 480

Arg Leu Asp Ile Lys His Asn Arg Pro Arg Arg Asp Cys Gly Glu Gly
                       485                 490                 495

Lys Gly Leu Leu Gly Gly Glu Asn Glu Ser Gly Arg Arg Gly Leu
                   500                 505                 510

Lys Gly Leu Phe Cys Pro Arg Arg Gly Ser Arg Val Glu Gly Trp Asn
               515                 520                 525

Gln Gly Glu Gly Gly Cys
           530

<210> SEQ ID NO 7
<211> LENGTH: 1320
<212> TYPE: DNA
<213> ORGANISM: Homo sapiens
<220> FEATURE:
<221> NAME/KEY: CDS
<222> LOCATION: (61)..(1260)

<400> SEQUENCE: 7
cgggcccccc ctcgaggtcg ggccggactt ggctgggctc ccttcaccct ctgcggagtc      60 atg agg gcg aac gac gct ctg cag gtg ctg ggc ttg ctt ttc agc ctg      108
Met Arg Ala Asn Asp Ala Leu Gln Val Leu Gly Leu Leu Phe Ser Leu
1               5                   10                  15 gcc cgg ggc tcc gag gtg ggc aac tct cag gca gtg tgt cct ggg act      156
Ala Arg Gly Ser Glu Val Gly Asn Ser Gln Ala Val Cys Pro Gly Thr
                20                  25                  30 ctg aat ggc ctg agt gtg acc ggc gat gct gag aac caa tac cag aca      204
Leu Asn Gly Leu Ser Val Thr Gly Asp Ala Glu Asn Gln Tyr Gln Thr
            35                  40                  45 ctg tac aag ctc tac gag agg tgt gag gtg gtg atg ggg aac ctt gag      252
Leu Tyr Lys Leu Tyr Glu Arg Cys Glu Val Val Met Gly Asn Leu Glu
        50                  55                  60 att gtg ctc acg gga cac aat gcc gac ctc tcc ttc ctg cag tgg att      300
Ile Val Leu Thr Gly His Asn Ala Asp Leu Ser Phe Leu Gln Trp Ile
65                  70                  75                  80 cga gaa gtg aca ggc tat gtc ctc gtg gcc atg aat gaa ttc tct act      348
Arg Glu Val Thr Gly Tyr Val Leu Val Ala Met Asn Glu Phe Ser Thr
                85                  90                  95 cta cca ttg ccc aac ctc cgc gtg gtg cga ggg acc cag gtc tac gat      396
Leu Pro Leu Pro Asn Leu Arg Val Val Arg Gly Thr Gln Val Tyr Asp
                100                 105                 110 ggg aag ttt gcc atc ttc gtc atg ttg aac tat aac acc aac tcc agc      444
Gly Lys Phe Ala Ile Phe Val Met Leu Asn Tyr Asn Thr Asn Ser Ser
            115                 120                 125 cac gct ctg cgc cag ctc cgc ttg act cag ctc acc gag att ctg tca      492
His Ala Leu Arg Gln Leu Arg Leu Thr Gln Leu Thr Glu Ile Leu Ser
        130                 135                 140 ggg ggt gtt tat att gag aag aac gat aag ctt tgt cac atg gac aca      540
Gly Gly Val Tyr Ile Glu Lys Asn Asp Lys Leu Cys His Met Asp Thr
145                 150                 155                 160
```

-continued

| | | |
|---|---|---|
| att gac tgg agg gac atc gtg agg gac cga gat gct gag ata gtg gtg<br>Ile Asp Trp Arg Asp Ile Val Arg Asp Arg Asp Ala Glu Ile Val Val<br>165                    170                    175 | 588 |
| aag gac aat ggc aga agc tgt ccc ccc tgt cat gag gtt tgc aag ggg<br>Lys Asp Asn Gly Arg Ser Cys Pro Pro Cys His Glu Val Cys Lys Gly<br>    180                    185                    190 | 636 |
| cga tgc tgg ggt cct gga tca gaa gac tgc cag aca ttg acc aag acc<br>Arg Cys Trp Gly Pro Gly Ser Glu Asp Cys Gln Thr Leu Thr Lys Thr<br>        195                    200                    205 | 684 |
| atc tgt gct cct cag tgt aat ggt cac tgc ttt ggg ccc aac ccc aac<br>Ile Cys Ala Pro Gln Cys Asn Gly His Cys Phe Gly Pro Asn Pro Asn<br>210                    215                    220 | 732 |
| cag tgc tgc cat gat gag tgt gcc ggg ggc tgc tca ggc cct cag gac<br>Gln Cys Cys His Asp Glu Cys Ala Gly Gly Cys Ser Gly Pro Gln Asp<br>225                    230                    235                    240 | 780 |
| aca gac tgc ttt gcc tgc cgg cac ttc aat gac agt gga gcc tgt gta<br>Thr Asp Cys Phe Ala Cys Arg His Phe Asn Asp Ser Gly Ala Cys Val<br>                245                    250                    255 | 828 |
| cct cgc tgt cca cag cct ctt gtc tac aac aag cta act ttc cag ctg<br>Pro Arg Cys Pro Gln Pro Leu Val Tyr Asn Lys Leu Thr Phe Gln Leu<br>            260                    265                    270 | 876 |
| gaa ccc aat ccc cac acc aag tat cag tat gga gga gtt tgt gta gcc<br>Glu Pro Asn Pro His Thr Lys Tyr Gln Tyr Gly Gly Val Cys Val Ala<br>275                    280                    285 | 924 |
| agc tgt ccc cat aac ttt gtg gtg gat caa aca tcc tgt gtc agg gcc<br>Ser Cys Pro His Asn Phe Val Val Asp Gln Thr Ser Cys Val Arg Ala<br>    290                    295                    300 | 972 |
| tgt cct cct gac aag atg gaa gta gat aaa aat ggg ctc aag atg tgt<br>Cys Pro Pro Asp Lys Met Glu Val Asp Lys Asn Gly Leu Lys Met Cys<br>305                    310                    315                    320 | 1020 |
| gag cct tgt ggg gga cta tgt ccc aaa gcc tgt gag gga aca ggc tct<br>Glu Pro Cys Gly Gly Leu Cys Pro Lys Ala Cys Glu Gly Thr Gly Ser<br>        325                    330                    335 | 1068 |
| ggg agc cgc ttc cag act gtg gac tcg agc aac att gat gga ttt gtg<br>Gly Ser Arg Phe Gln Thr Val Asp Ser Ser Asn Ile Asp Gly Phe Val<br>            340                    345                    350 | 1116 |
| aac tgc acc aag atc ctg ggc aac ctg gac ttt ctg atc acc ggc ctc<br>Asn Cys Thr Lys Ile Leu Gly Asn Leu Asp Phe Leu Ile Thr Gly Leu<br>355                    360                    365 | 1164 |
| aat ggg tta gag atc ctg cct tcc ctc ctt aga ccc cag ccc acg cac<br>Asn Gly Leu Glu Ile Leu Pro Ser Leu Leu Arg Pro Gln Pro Thr His<br>    370                    375                    380 | 1212 |
| ccc tca cag ttc att tca ttg gcc aaa act ttc cta tgt gga gct gac<br>Pro Ser Gln Phe Ile Ser Leu Ala Lys Thr Phe Leu Cys Gly Ala Asp<br>385                    390                    395                    400 | 1260 |
| taggaatcaa agtcataaaa ttctagcctg ttaaaaaaaa aaaaaaaaaa aaaaaaaaaa | 1320 |

<210> SEQ ID NO 8
<211> LENGTH: 400
<212> TYPE: PRT
<213> ORGANISM: Homo sapiens

<400> SEQUENCE: 8

Met Arg Ala Asn Asp Ala Leu Gln Val Leu Gly Leu Leu Phe Ser Leu
1                 5                      10                    15

Ala Arg Gly Ser Glu Val Gly Asn Ser Gln Ala Val Cys Pro Gly Thr
                  20                    25                    30

Leu Asn Gly Leu Ser Val Thr Gly Asp Ala Glu Asn Gln Tyr Gln Thr
        35                    40                    45

```
Leu Tyr Lys Leu Tyr Glu Arg Cys Glu Val Val Met Gly Asn Leu Glu
     50                  55                  60
Ile Val Leu Thr Gly His Asn Ala Asp Leu Ser Phe Leu Gln Trp Ile
 65                  70                  75                  80
Arg Glu Val Thr Gly Tyr Val Leu Val Ala Met Asn Glu Phe Ser Thr
                 85                  90                  95
Leu Pro Leu Pro Asn Leu Arg Val Val Arg Gly Thr Gln Val Tyr Asp
             100                 105                 110
Gly Lys Phe Ala Ile Phe Val Met Leu Asn Tyr Asn Thr Asn Ser Ser
             115                 120                 125
His Ala Leu Arg Gln Leu Arg Leu Thr Gln Leu Thr Glu Ile Leu Ser
    130                 135                 140
Gly Gly Val Tyr Ile Glu Lys Asn Asp Lys Leu Cys His Met Asp Thr
145                 150                 155                 160
Ile Asp Trp Arg Asp Ile Val Arg Asp Arg Asp Ala Glu Ile Val Val
            165                 170                 175
Lys Asp Asn Gly Arg Ser Cys Pro Pro Cys His Glu Val Cys Lys Gly
            180                 185                 190
Arg Cys Trp Gly Pro Gly Ser Glu Asp Cys Gln Thr Leu Thr Lys Thr
        195                 200                 205
Ile Cys Ala Pro Gln Cys Asn Gly His Cys Phe Gly Pro Asn Pro Asn
210                 215                 220
Gln Cys Cys His Asp Glu Cys Ala Gly Gly Cys Ser Gly Pro Gln Asp
225                 230                 235                 240
Thr Asp Cys Phe Ala Cys Arg His Phe Asn Asp Ser Gly Ala Cys Val
                245                 250                 255
Pro Arg Cys Pro Gln Pro Leu Val Tyr Asn Lys Leu Thr Phe Gln Leu
            260                 265                 270
Glu Pro Asn Pro His Thr Lys Tyr Gln Tyr Gly Gly Val Cys Val Ala
            275                 280                 285
Ser Cys Pro His Asn Phe Val Val Asp Gln Thr Ser Cys Val Arg Ala
    290                 295                 300
Cys Pro Pro Asp Lys Met Glu Val Asp Lys Asn Gly Leu Lys Met Cys
305                 310                 315                 320
Glu Pro Cys Gly Gly Leu Cys Pro Lys Ala Cys Glu Gly Thr Gly Ser
                325                 330                 335
Gly Ser Arg Phe Gln Thr Val Asp Ser Ser Asn Ile Asp Gly Phe Val
            340                 345                 350
Asn Cys Thr Lys Ile Leu Gly Asn Leu Asp Phe Leu Ile Thr Gly Leu
            355                 360                 365
Asn Gly Leu Glu Ile Leu Pro Ser Leu Leu Arg Pro Gln Pro Thr His
    370                 375                 380
Pro Ser Gln Phe Ile Ser Leu Ala Lys Thr Phe Leu Cys Gly Ala Asp
385                 390                 395                 400
```